United States Patent
Wisbey et al.

(10) Patent No.: US 9,864,843 B2
(45) Date of Patent: Jan. 9, 2018

(54) SYSTEM AND METHOD FOR IDENTIFYING PERFORMANCE DAYS

(71) Applicant: LOGITECH EUROPE, S.A., Lausanne (CH)

(72) Inventors: Ben Wisbey, Canberra (AU); David Shepherd, Canberra (AU)

(73) Assignee: Logitech Europe S.A., Lausanne (CH)

( * ) Notice: Subject to any disclaimer, the term of this patent is extended or adjusted under 35 U.S.C. 154(b) by 1051 days.

(21) Appl. No.: 14/140,411

(22) Filed: Dec. 24, 2013

(65) Prior Publication Data
US 2015/0120018 A1    Apr. 30, 2015

Related U.S. Application Data

(63) Continuation-in-part of application No. 14/137,734, filed on Dec. 20, 2013, now abandoned, which is a continuation-in-part of application No. 14/062,815, filed on Oct. 24, 2013, now abandoned.

(51) Int. Cl.
*A61B 5/04* (2006.01)
*G06F 19/00* (2011.01)

(52) U.S. Cl.
CPC ................ *G06F 19/3481* (2013.01)

(58) Field of Classification Search
CPC ... G06F 19/3481; Y10S 482/00; A63B 24/00; A63B 2230/00
USPC ............ 600/508, 509, 513, 516, 520, 521; 607/77; 482/148
See application file for complete search history.

(56) References Cited

U.S. PATENT DOCUMENTS

| | | | |
|---|---|---|---|
| 2,189,096 | A | 2/1940 | Alonge |
| 3,543,724 | A | 12/1970 | Kirkpatrick et al. |
| 3,978,849 | A | 9/1976 | Geneen |
| 4,129,124 | A | 12/1978 | Thalmann |
| 4,224,984 | A | 9/1980 | Cramer et al. |
| 4,307,727 | A | 12/1981 | Haynes |
| 4,331,154 | A | 5/1982 | Broadwater et al. |
| 4,407,295 | A | 10/1983 | Steuer et al. |
| 4,409,983 | A | 10/1983 | Albert |

(Continued)

OTHER PUBLICATIONS

"Watch Stylish Blue Light LED Round Dial Matrix Stainless from ChinaBuye.com" by YnopoB. YouTube [dated Apr. 23, 2012][online][retrieved on Dec. 31, 2015] (https://www.youtube.com/watch?v=e_LWbXHvvWg).

(Continued)

*Primary Examiner* — Michael Carey
(74) *Attorney, Agent, or Firm* — Patterson + Sheridan LLP

(57) ABSTRACT

Systems and methods for identifying and presenting information regarding performance periods are provided. Fatigue level associated with fatigue experienced in response to a stimulus and recovery from such fatigue may be determined based on heart rate variability (HRV) data and learned user characteristics. One or more cycles of fatigue and recovery can be identified as a fitness cycle(s), each fitness cycle encompassing a period of time beginning with the stimulus associated with the fitness-related activity and progressing through recovery from the fatigue experienced in response to the stimulus associated with the fitness-related activity. A performance period may be predicted based on a predetermined fatigue/recovery level instance within a fitness cycle.

19 Claims, 14 Drawing Sheets

(56) References Cited

U.S. PATENT DOCUMENTS

| | | | |
|---|---|---|---|
| 4,491,970 A | 1/1985 | Lawhite et al. | |
| 5,301,154 A | 4/1994 | Suga | |
| 5,392,261 A | 2/1995 | Hsu | |
| 5,406,952 A | 4/1995 | Barnes et al. | |
| 5,524,637 A | 6/1996 | Erickson | |
| 5,734,625 A | 3/1998 | Kondo | |
| 5,755,623 A | 5/1998 | Mizenko | |
| 5,899,370 A | 5/1999 | Bould | |
| 6,151,968 A | 11/2000 | Chou | |
| 6,361,503 B1 | 3/2002 | Starobin et al. | |
| 6,736,759 B1 | 5/2004 | Stubbs et al. | |
| 7,192,401 B2 | 3/2007 | Saalasti et al. | |
| 7,717,827 B2 | 5/2010 | Kurunmaki et al. | |
| 7,914,425 B2 | 3/2011 | Hanoun | |
| 8,992,385 B2 | 3/2015 | Lemos | |
| 9,223,936 B2* | 12/2015 | Aragones | G06F 19/3481 |
| 2002/0151811 A1 | 10/2002 | Starobin et al. | |
| 2002/0188210 A1 | 12/2002 | Aizawa | |
| 2003/0065269 A1 | 4/2003 | Vetter et al. | |
| 2005/0056655 A1 | 3/2005 | Gary | |
| 2005/0116811 A1 | 6/2005 | Eros et al. | |
| 2005/0256416 A1 | 11/2005 | Chen | |
| 2006/0079800 A1* | 4/2006 | Martikka | A61B 5/0488 600/546 |
| 2006/0183980 A1 | 8/2006 | Yang | |
| 2007/0118043 A1 | 5/2007 | Oliver et al. | |
| 2008/0132383 A1 | 6/2008 | Einav et al. | |
| 2008/0228089 A1 | 9/2008 | Cho et al. | |
| 2009/0105560 A1* | 4/2009 | Solomon | A61B 5/0002 600/301 |
| 2009/0312656 A1 | 12/2009 | Lau et al. | |
| 2010/0197463 A1 | 8/2010 | Haughay, Jr. et al. | |
| 2011/0021319 A1 | 1/2011 | Nissila et al. | |
| 2011/0092790 A1 | 4/2011 | Wilder-Smith et al. | |
| 2011/0260870 A1 | 10/2011 | Bailey | |
| 2012/0022341 A1 | 1/2012 | Zdeblick | |
| 2012/0168471 A1 | 7/2012 | Wilson | |
| 2012/0253485 A1 | 10/2012 | Weast et al. | |
| 2013/0064049 A1 | 3/2013 | Pileri et al. | |
| 2013/0237778 A1 | 9/2013 | Rouquette | |
| 2014/0032234 A1 | 1/2014 | Anderson | |
| 2014/0073486 A1 | 3/2014 | Ahmed et al. | |
| 2014/0107493 A1 | 4/2014 | Yuen et al. | |
| 2014/0228175 A1 | 8/2014 | Lemos et al. | |

OTHER PUBLICATIONS

"Elite Clock Military Style LED Watch" by ledwatchsuk. YouTube [dated May 31, 2011][online][retrieved on Aug. 14, 2015].

* cited by examiner

| | | Reference Activity Instensity (RAI) | | | | | |
|---|---|---|---|---|---|---|---|
| | | RAI_0 | RAI_1 | RAI_2 | RAI_3 | RAI_4 | RAI_5 |
| Reference Activity Type (RAT) | RAT_0 | ML_0,0 | ML_0,1 | ML_0,2 | ML_0,3 | ML_0,4 | ML_0,5 |
| | RAT_1 | ML_1,0 | ML_1,1 | ML_1,2 | ML_1,3 | ML_1,4 | ML_1,5 |
| | RAT_2 | ML_2,0 | ML_2,1 | ML_2,2 | ML_2,3 | ML_2,4 | ML_2,5 |
| | RAT_3 | ML_3,0 | ML_3,1 | ML_3,2 | ML_3,3 | ML_3,4 | ML_3,5 |
| | RAT_4 | ML_4,0 | ML_4,1 | ML_4,2 | ML_4,3 | ML_4,4 | ML_4,5 |
| | RAT_5 | ML_5,0 | ML_5,1 | ML_5,2 | ML_5,3 | ML_5,4 | ML_5,5 |

| | | Frequency of Movement (F) | | | | | |
|---|---|---|---|---|---|---|---|
| 1084 | | | F_0 | F_1 | F_2 | F_3 | F_4 | F_5 |
| | Reference Activity Type (RAT) | RAT_0 | RAI_0,0 | RAI_0,1 | RAI_0,2 | RAI_0,3 | RAI_0,4 | RAI_0,5 |
| | | RAI_2 | RAI_2,0 | RAI_2,1 | RAI_2,2 | RAI_2,3 | RAI_2,4 | RAI_2,5 |
| | | RAI_3 | RAI_3,0 | RAI_3,1 | RAI_3,2 | RAI_3,3 | RAI_3,4 | RAI_3,5 |
| | | RAI_4 | RAI_4,0 | RAI_4,1 | RAI_4,2 | RAI_4,3 | RAI_4,4 | RAI_4,5 |
| | | RAI_5 | RAI_5,0 | RAI_5,1 | RAI_5,2 | RAI_5,3 | RAI_5,4 | RAI_5,5 |

| Date | MAS | Avg. UAI | Sleep Time (hours) | Fatigue Level |
|---|---|---|---|---|
| 1 Nov. 2013 | 2,500 | 7 | 6 | HIGH |
| 2 Nov. 2013 | 2,000 | 5 | 8 | NORMAL |
| 3 Nov. 2013 | 1,500 | 3 | 9 | LOW |

Fig. 10D

SYSTEM AND METHOD FOR IDENTIFYING PERFORMANCE DAYS

CROSS-REFERENCE TO RELATED APPLICATIONS

This application is a continuation-in-part of and claims the benefit of U.S. patent application Ser. No. 14/137,734, filed Dec. 20, 2013, titled "System and Method for Providing a Smart Activity Score," (published as US2015-0119760A1 with examination pending in the USPTO as of May 1, 2017), which is a continuation-in-part of U.S. patent application Ser. No. 14/062,815, filed Oct. 24, 2013, titled "Wristband with Removable Activity Monitoring Device" (published as US2015-0116125 with examination abandoned as of Jan. 27, 2017). The contents of both the Ser. No. 14/137,734 application and the Ser. No. 14/062,815 application are incorporated herein by reference.

TECHNICAL FIELD

The present disclosure relates generally to fitness monitoring devices, and more particularly to a system and method for providing an interpreted recovery score.

DESCRIPTION OF THE RELATED ART

Previous generation movement monitoring and fitness tracking devices generally enabled only a tracking of activity that accounts for total calories burned based on universal metabolic equivalent tasks. Currently available fitness tracking devices now add functionality that customizes metabolic equivalent tasks according to user characteristics. One issue with currently available fitness tracking devices is that they do not account for the performance or recovery state of the user in a scientific, user-specific way. Another issue is that currently available solutions do not account in a precise manner for the optimal relationship between activity and recovery.

BRIEF SUMMARY OF THE DISCLOSURE

In view of the above drawbacks, there exists a long-felt need for fitness monitoring devices that detect a fatigue level in a scientific way and provide user-specific recovery feedback based on actual, historical data. Furthermore, there is a need for fitness monitoring devices that provide increased resolution into the optimal balance between recovery and activity such that users can identify such periods (e.g., days) when they may achieve optimal performance when engaging in one or more activities.

Embodiments of the present disclosure include systems and methods for identifying periods when a user may achieve optimal performance when engaging in one or more activities.

One embodiment involves an apparatus for identifying a performance period. The apparatus comprises a fitness cycle identification module that identifies progression through a plurality of fitness cycles, each of the plurality of fitness cycles encompassing a period from the beginning of a stimulus through recovery from the stimulus. The apparatus further comprises a performance period identification module that predicts optimal performance periods based on the plurality of fitness cycles.

In another embodiment, the apparatus further comprises a fatigue level module that detects a fatigue level occurring in response to the stimulus. Additionally, the apparatus may comprise a recovery module that determines a recovery level based at least in part, on the fatigue level. Further still, the apparatus may comprise an archive for storing learned user characteristics including at least a fatigue profile of a user. The fatigue level module and the recovery module detect the fatigue level and determine the recovery level, respectively, based upon heart rate variability and the learned user characteristics.

In a further embodiment, the fitness cycle identification module presents data associated with the plurality of fitness cycles in at least one of a numerical, descriptive, or visual manner. The plurality of fitness cycles are either contiguous or non-contiguous in time.

In one embodiment, the performance period identification module predicts the optimal performance periods by determining periods of time predicted to occur within each of the plurality of fitness cycles during which experiencing additional stimuli promotes future increased fitness levels.

Another embodiment involves a method of identifying a performance period. The method comprises determining heart rate variability data of a user; identifying a fitness cycle comprising a period of time beginning from a stimulus and progressing through recovery from fatigue experienced in response to the stimulus based on the heart rate variability data and learned user characteristics; and determining an optimal performance period within the fitness cycle.

In one embodiment, the method further comprises detecting a fatigue level associated with the fatigue experienced in response to the stimulus. The determining of the optimal performance period comprises determining a period during which the fatigue experienced falls within a range of fatigue level values corresponding to a period of recovery within the fitness cycle.

In another embodiment, the method comprises determining a recovery level based at least in part, on the fatigue level. The fatigue level can be periodically detected to determine the recovery level.

In a further embodiment, the method comprises presenting data associated with the fitness cycle in at least one of a numerical, descriptive, or visual manner. Presenting data associated with the optimal performance period can be done in conjunction with the data associated with the fitness cycle.

One embodiment involves a system for identifying a performance period. The system comprises a processor, and a non-transitory computer readable medium including computer program code. The non-transitory computer readable medium and the computer program code is adapted to, with the processor, cause the system to: detect a fatigue level associated with fatigue experienced in response to a stimulus; determine a recovery level based at least in part, on the fatigue level; identify a fitness cycle, the fitness cycle comprising a segment of time beginning from the stimulus and progressing through recovery from the fatigue experienced in response to the stimulus; and predict an optimal performance period based on the identification of the fitness cycle.

In one embodiment, the non-transitory computer readable medium and the computer program code adapted to, with the processor, further cause the system to monitor a movement to determine if the movement is indicative of the stimulus. The non-transitory computer readable medium and the computer program code adapted to, with the processor, cause the system to detect the fatigue level and determine recovery level based on heart rate variability data and learned user characteristics.

In another embodiment, the non-transitory computer readable medium and the computer program code adapted to, with the processor, further cause the system to present data associated with the fatigue level, and the recovery level to characterize the identified fitness cycle in at least one of a numerical, descriptive, or visual manner. In a further embodiment, the non-transitory computer readable medium and the computer program code adapted to, with the processor, further cause the system to present data associated with the optimal performance period in conjunction with the data characterizing the identified fitness cycle.

Other features and aspects of the disclosure will become apparent from the following detailed description, taken in conjunction with the accompanying drawings, which illustrate, by way of example, the features in accordance with embodiments of the disclosure. The summary is not intended to limit the scope of the disclosure, which is defined solely by the claims attached hereto.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments of the disclosure.

FIG. 10B is an example of a metabolic loading table.

FIG. 10C is an example of an activity intensity library.

FIG. 10D is an example of an archive table.

The figures are not intended to be exhaustive or to limit the disclosure to the precise form disclosed. It should be understood that the disclosure can be practiced with modification and alteration, and that the disclosure can be limited only by the claims and the equivalents thereof.

DETAILED DESCRIPTION

Embodiments of the present disclosure are directed toward systems and methods for identifying performance periods. In one such embodiment, the systems and methods are directed to a device for identifying performance periods. According to some embodiments of the disclosure, the device may be an electronic capsule embedded in and removable from an attachable device that may be attached to a user. In one embodiment, the attachable device is a wristband that includes an activity monitoring device.

Figure 1:
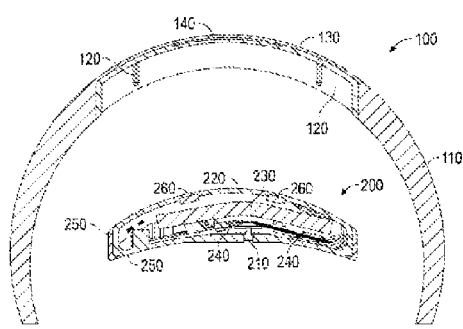
FIG. 1 illustrates a cross-sectional view of the wristband and electronic modules of an example activity monitoring device.

FIG. 1 is a diagram illustrating a cross-sectional view of an exemplary embodiment of an activity monitoring device. Referring now to FIG. 1, an activity monitoring device comprises an electronic capsule 200 and a wristband 100. Electronic capsule 200 comprises wrist biosensor 210, finger biosensor 220, battery 230, one or more logic circuits 240, and casing 250.

In some embodiments, one or more logic circuits 240 comprise an accelerometer, a wireless transmitter, and circuitry. Logic circuits 240 may further comprise a gyroscope. Logic circuits 240 may be configured to process electronic input signals from the biosensors and the accelerometer, store the processed signals as data, and output the data using the wireless transmitter. The transmitter is configured to communicate using available wireless communications standards. For example, in some embodiments, the wireless transmitter may be a BLUETOOTH® transmitter, a Wi-Fi transmitter, a GPS transmitter, a cellular transmitter, or some combination thereof. In an alternative embodiment, the wireless transmitter further comprises a wired interface (e.g. USB, fiber optic, HDMI, etc.) for communicating stored data.

Logic circuits 240 are electrically coupled to wrist biosensor 210 and finger biosensor 220. In addition, logic circuits 240 are configured to receive and process a plurality of electric signals from each of wrist biosensor 210 and finger biosensor 220. In some embodiments, the plurality of electric signals comprise an activation time signal and a recovery time signal such that logic circuits 240 may process the plurality of signals to calculate an activation recovery interval equal to the difference between the activation time signal and the recovery time signal. In some embodiments, the plurality of signals may comprise electro-cardio signals from a heart, and the logic circuits may process the electro-cardio signals to calculate and store a RR-interval, and the RR-interval may be used to calculate and store a heart rate variability (HRV) value. Here, the RR-interval is equal to the delta in time between two R-waves, where the R-waves are the electro-cardio signals generated by a ventricle contraction in the heart.

In some embodiments, logic circuits 240 detect and store metrics such as the amount of physical activity, sleep, or rest over a recent period of time, or the amount of time without physical activity over a recent period of time. Logic circuits 240 may then use the HRV, or the HRV in combination with said metrics, to calculate a fatigue level. In one embodiment, the fatigue level is a function of the recovery interval. Logic circuits 240 may detect, for example, the amount of physical activity and the amount of sleep a user experienced over the last 48 hours, combine those metrics with the user's HRV, and calculate a fatigue level of between 1 and 10, wherein the fatigue level could indicate the user's physical condition and aptitude for further physical activity that day. The fatigue level may also be calculated on a scale of between 1 and 100, or any other scale or range. In one embodiment, the typical fatigue level ranges from about 40 to 60. The fatigue level may also be represented on a descriptive scale; for example, low, normal, and high.

In some embodiments, finger biosensor 220 and wrist biosensor 210 are replaced or supplemented by a single biosensor. The single biosensor, in on embodiment, is an optical biosensor such as a pulse oximeter configured to detect blood oxygen saturation levels. The pulse oximeter may then output a signal to logic circuits 240 indicating detected a cardiac cycle phase, and the logic circuits may use cardiac cycle phase data to calculate a HRV value.

Wristband 100 comprises material 110 configured to encircle a human wrist. In one embodiment, wristband 100 is adjustable. Cavity 120 is notched on the radially inward facing side of the wristband and shaped to substantially the same dimensions as the profile of electronic capsule 200. In addition, aperture 130 is located in material 110 within cavity 120. Aperture 130 is shaped to substantially the same dimensions as the profile of finger biosensor 220. The combination of cavity 120 and aperture 130 is designed to detachably couple to electric capsule 200 such that, when electric capsule 200 is positioned inside cavity 120, finger biosensor 220 protrudes through aperture 130. Electronic capsule 200 may further comprise one or more magnets 260 configured to secure electronic capsule 200 to cavity 120. Magnets 260 may be concealed in casing 250. Alternatively, cavity 120 may be configured to conceal magnets 260 when electric capsule 200 detachably couples to the combination of cavity 120 and aperture 130.

Wristband 100 may further comprise steel strip 140 concealed in material 110 within cavity 120. In this embodiment, when electronic capsule 200 is positioned within cavity 120, one or more magnets 260 are attracted to steel strip 140, and pull electronic capsule 200 radially outward with respect to the wristband 100. The force provided by magnets 260 may detachably secure electronic capsule 200 inside cavity 120. In alternative embodiments, the electronic capsule 200 is positioned inside cavity 120, and affixed using a form-fit, snap-fit, press-fit, friction-fit, or VEL-CRO®, or other temporary adhesion or attachment technology.

Figure 3:
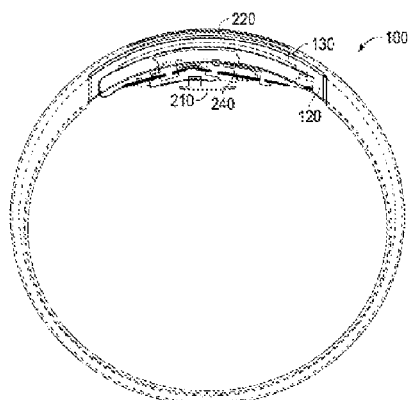
FIG. 3 illustrates a cross-sectional view of an example assembled activity monitoring device.
Figure 2:
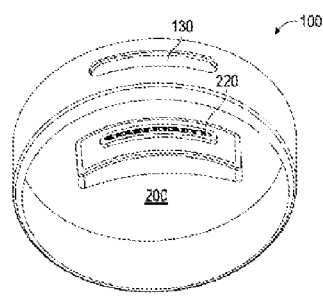
FIG. 2 illustrates a perspective view of an example activity monitoring device.
Figure 4:
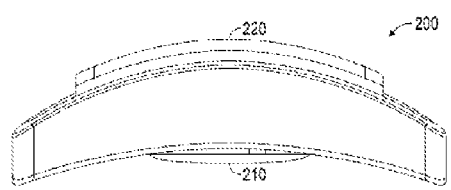
FIG. 4 illustrates a side view of an example electronic capsule.
Figure 5:
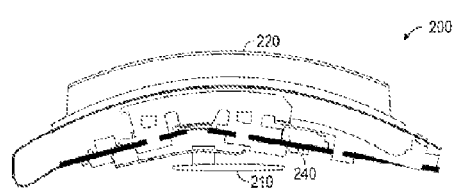
FIG. 5 illustrates a cross-sectional view of an example electronic capsule.
Figure 6:
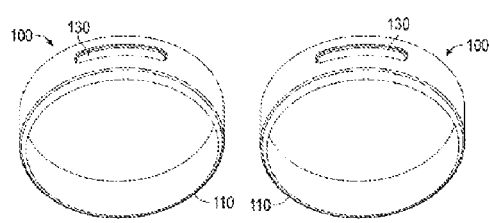
FIG. 6 illustrates perspective views of wristbands as used in one embodiment of the disclosed activity monitoring device.

FIG. 2 illustrates a perspective view of one embodiment of the disclosed activity monitoring device, in which wristband 100 and electronic capsule 200 are unassembled. FIG. 3 illustrates a cross-sectional view of one embodiment of a fully assembled wristband 100 with removable athletic monitoring device. FIG. 4 illustrates a side view of electronic capsule 200 according to one embodiment of the disclosure. FIG. 5 illustrates a cross-sectional view of electronic capsule 200. FIG. 6 is a perspective view of two possible variants of wristband 100 according to some embodiments of the disclosure. Wristbands 100 may be constructed with different dimensions, including different diameters, widths, and thicknesses, in order to accommodate different human wrist sizes and different preferences.

In some embodiments of the disclosure, electronic capsule 200 is detachably coupled to a cavity on a shoe and/or a sock. In other embodiments, electronic capsule 200 may be detachably coupled to sports equipment. For example, electronic capsule 200 may be detachably coupled to a skateboard, a bicycle, a helmet, a surfboard, a paddle boat, a body board, a hang glider, or other piece of sports equipment. In these embodiments, electronic capsule 200 is affixed to the sports equipment using magnets. Alternatively, in other embodiments, electronic capsule 200 is affixed using a form-fit, snap-fit, press-fit, friction-fit, suction cup, VEL-CRO®, or other technology that would be apparent to one of ordinary skill in the art.

Electronic capsule 200, in one embodiment of the disclosure, further comprises an optical sensor such as a heart rate sensor or oximeter. In this embodiment, the optical sensor is positioned to face radially inward towards a human wrist when the wristband is fit on the human wrist. Additionally, the optical sensor may be separate from electronic capsule 200, but still detachably coupled to wristband 100 and electronically coupled to the circuit boards enclosed in electronic capsule 200. Wristband 100 and electronic capsule 200 may operate in conjunction with a system for providing an interpreted recovery score.

Figure 7:
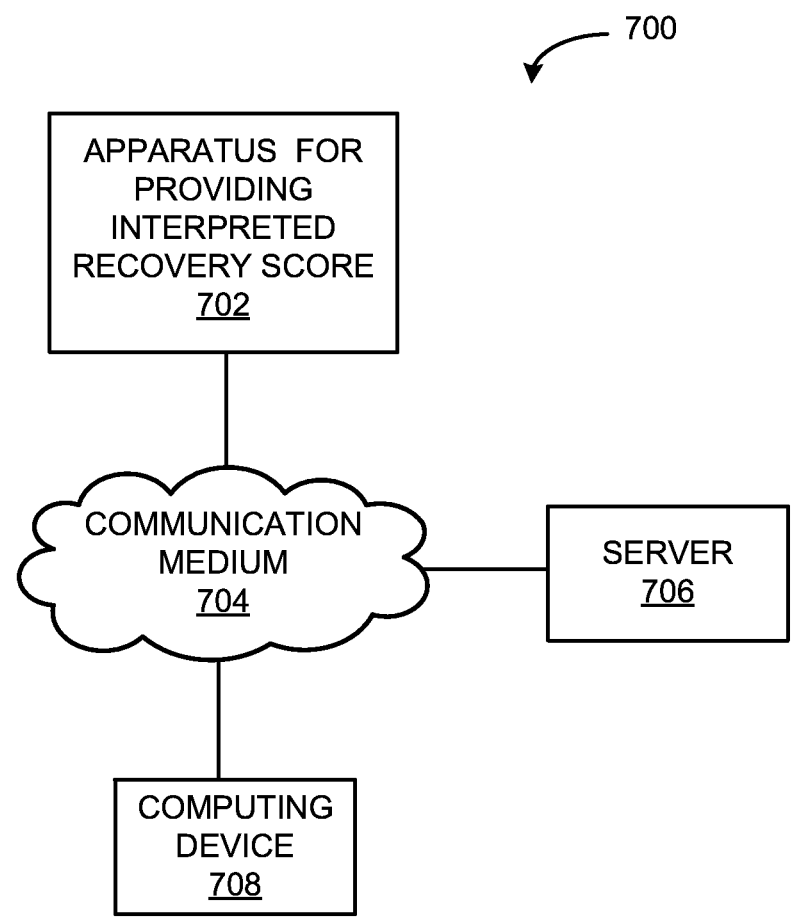
FIG. 7 illustrates an example system for providing an interpreted recovery score.

FIG. 7 is a schematic block diagram illustrating an example of system 700 for providing an interpreted recovery score. System 700 includes apparatus for providing interpreted recovery score 702, communication medium 704, server 706, and computing device 708.

Communication medium 704 may be implemented in a variety of forms. For example, communication medium 704 may be an Internet connection, such as a local area network ("LAN"), a wide area network ("WAN"), a fiber optic network, internet over power lines, a hard-wired connection (e.g., a bus), and the like, or any other kind of network connection. Communication medium 704 may be implemented using any combination of routers, cables, modems, switches, fiber optics, wires, radio, and the like. Communication medium 704 may be implemented using various wireless standards, including, but not limited to BLUETOOTH®, Wi-Fi, 4G LTE, etc. Still other known or otherwise appropriate methods or mechanisms for implementing communication medium 704 for communication purposes are contemplated herein.

Server 706 directs communications made over communication medium 704. Server 706 may be, for example, an Internet server, a router, a desktop or laptop computer, a smartphone, a tablet, a processor, a module, or the like. In one embodiment, server 706 directs communications between communication medium 704 and computing device 708. For example, server 706 may update information stored on computing device 708, or server 706 may send information to computing device 708 in real time.

Computing device 708 may take a variety of forms, such as a desktop or laptop computer, a smartphone, a tablet, a processor, a module, or the like. In addition, computing device 708 may be a processor or module embedded in a wearable sensor, a bracelets, a smart-watch, a piece of clothing, an accessory, and so on. For example, computing device 708 may be substantially similar to devices embedded in electronic capsule 200, which may be embedded in and removable from wristband 100, as illustrated in FIG. 1. Computing device 708 may communicate with other devices over communication medium 704 with or without the use of server 706. In one embodiment, computing device 708 includes apparatus 702. In various embodiments, apparatus 702 is used to perform various processes described herein.

Figure 8:
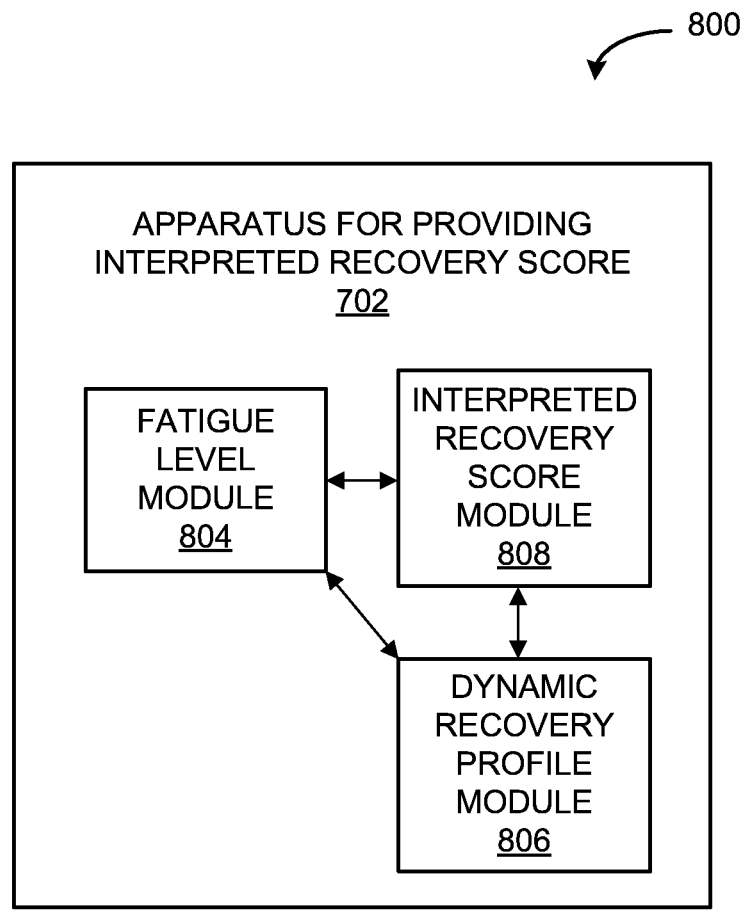
FIG. 8 illustrates an example apparatus for providing an interpreted recovery score.

FIG. 8 is a schematic block diagram illustrating one embodiment of an apparatus for providing an interpreted recovery score 800. Apparatus 800 includes apparatus 702 with fatigue level module 804, dynamic recovery profile module 806, and interpreted recovery score module 808.

In one embodiment of apparatus 800, a movement monitoring module (not shown) monitors a movement to create a metabolic activity score based on the movement and user information. The movement monitoring module will be described below in further detail with regard to various processes.

Fatigue level module 804 detects a fatigue level. Fatigue level module 804 will be described below in further detail with regard to various processes.

Dynamic recovery profile module 806 creates and updates a dynamic recovery profile based on an archive. The archive includes historical information about the fatigue level. In one embodiment, the archive includes historical information about the movement and the metabolic activity score. Dynamic recovery profile module 806 will be described below in further detail with regard to various processes.

Interpreted recovery score module 808 creates and updates an interpreted recovery score based on the fatigue level and the dynamic recovery profile. Interpreted recovery score module 808 will be described below in further detail with regard to various processes.

Figure 9:
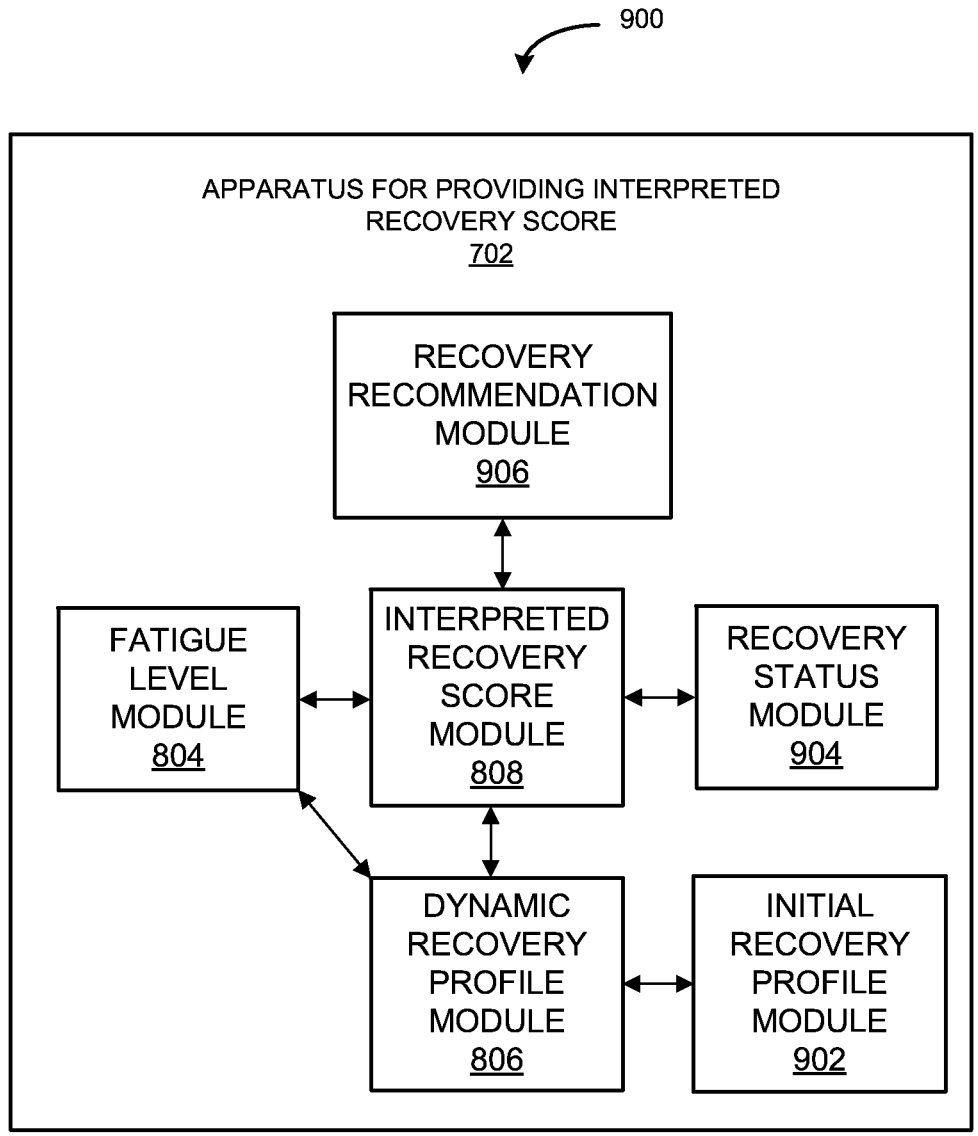
FIG. 9 illustrates another example apparatus for providing an interpreted recovery score.

FIG. 9 is a schematic block diagram illustrating one embodiment of apparatus for providing an interpreted recovery score 900. Apparatus 900 includes apparatus for providing an interpreted recovery score 702 with fatigue level module 804, dynamic recovery profile module 806, and interpreted recovery score module 808. Apparatus 900 also includes initial recovery profile module 902, recovery status module 904, and recovery recommendation module 906. Initial recovery profile module 902, recovery status module 904, and recovery recommendation module 906 will be described below in further detail with regard to various processes. In one embodiment, apparatus 900 also includes the movement monitoring module (not shown) described above with respect to FIG. 8.

In one embodiment, at least one of fatigue level module 804, dynamic recovery profile module 806, interpreted recovery score module 808, initial recovery profile module 902, recovery status module 904, and recovery recommendation module 906 are embodied in a wearable sensor, such as electronic capsule 200. In various embodiments, any of the modules described herein are embodied in electronic capsule 200 and connect to other modules described herein via communication medium 704. In other cases, the modules are embodiment in various other forms of hardware.

Figure 10A:
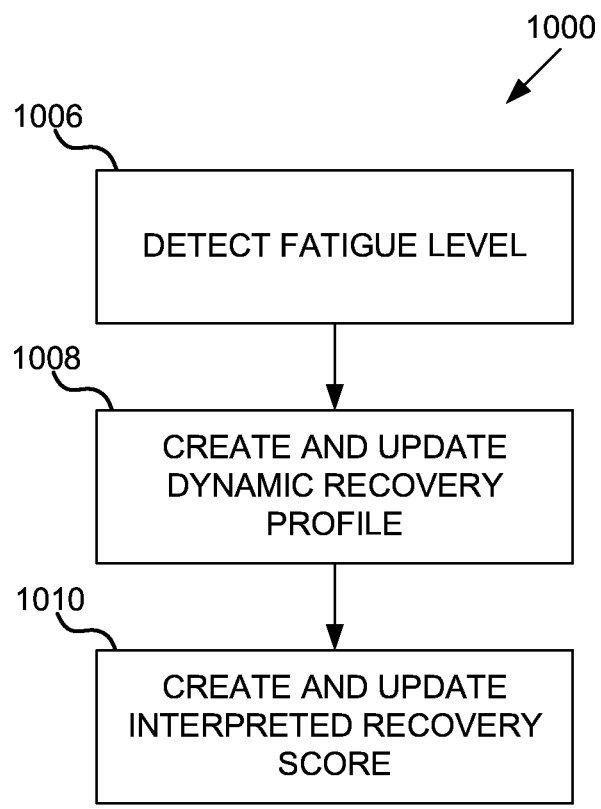
FIG. 10A is an operational flow diagram illustrating an example of a method for creating and updating an interpreted recovery score.

FIG. 10A is an operational flow diagram illustrating example method 1000 for providing an interpreted recovery score in accordance with an embodiment of the present disclosure. The operations of method 1000 create and update an interpreted recovery score based on a user's personalized fatigue levels, as recorded over time. In various embodiments, the fatigue level is based on a measured heart rate variability for the user and is a function of recovery. Moreover, the operations of method 1000 take into account not only the user's current fatigue level, but also the relationship between current and past fatigue levels to create an interpreted recovery score that accurately reflects the user's physical condition and performance capabilities. This aids in providing a personalized metric by which the user can attain peak performance. In one embodiment, apparatus 702, wristband 100, and electronic capsule 200 perform various operations of method 1000.

In one embodiment, movement is monitored to create a metabolic activity score based on the movement and user information. The metabolic activity score, in one embodiment, is created from a set of metabolic loadings. The metabolic loadings may be determined by identifying a user activity type from a set of reference activity types and by identifying a user activity intensity from a set of reference activity intensities. In addition, the metabolic loadings may be determined based on information provided by a user (user information).

User information may include, for example, an individual's height, weight, age, gender, and geographic and environmental conditions. The user may provide the user information by, for example, a user interface of computing device 708, or of electronic capsule 200. User information may be determined based on various measurements—for example, measurements of the user's body-fat content or body type. In addition, the user information may be determined, for example, by an altimeter or GPS, which may be used to determine the user's elevation, weather conditions in the user's environment, etc. In one embodiment, apparatus 702 obtains user information from the user indirectly. For example, apparatus 702 may collect the user information from a social media account, from a digital profile, or the like.

The user information, in one embodiment, includes a user lifestyle selected from a set of reference lifestyles. For example, apparatus 702 may prompt the user for information about the user's lifestyle (e.g., via a user interface). Apparatus 702 may prompt the user to determine how active the user's lifestyle is. Additionally, the user may be prompted to select a user lifestyle from a set of reference lifestyles. The reference lifestyles may include a range of lifestyles, for example, ranging from inactive, on one end, to highly active on the other end. In such a case, the reference lifestyles that the user selects from may include sedentary, mildly active, moderately active, and heavily active.

In one instance, the user lifestyle is determined from the user as an initial matter. For example, upon initiation, apparatus 702 may prompt the user to provide a user lifestyle. In a further embodiment, the user is prompted periodically to select a user lifestyle. In this fashion, the user lifestyle selected may be aligned with the user's actual activity level as the user's activity level varies over time. In another embodiment, the user lifestyle is updated without intervention from the user.

The metabolic loadings, in one embodiment, are numerical values and may represent a rate of calories burned per unit weight per unit time (e.g., having units of kcal per kilogram per hour). By way of example, the metabolic loadings may be represented in units of oxygen uptake (e.g., in milliliters per kilogram per minute). The metabolic loadings may also represent a ratio of the metabolic rate during activity (e.g., the metabolic rate associated with a particular activity type and/or an activity intensity) to the metabolic rate during rest. The metabolic loadings, may, for example be represented in a metabolic table, such as metabolic table 1050, illustrated in FIG. 10B. In one embodiment, the metabolic loadings are specific to the user information. For example, a metabolic loading may increase for a heavier user, or for an increased elevation, but may decrease for a lighter user or for a decreased elevation.

In one embodiment, the set of metabolic loadings are determined based on the user lifestyle, in addition to the other user information. For example, the metabolic loadings for a user with a heavily active lifestyle may differ from the metabolic loadings for a user with a sedentary lifestyle. In this fashion, there may be a greater coupling between the metabolic loadings and the user's characteristics.

In various embodiments, a device (e.g., computing device 708) or a module (e.g., electronic capsule 200 or a module therein) stores or provides the metabolic loadings. The metabolic loadings may be maintained or provided by server 706 or over communication medium 704. In one embodiment, a system administrator provides the metabolic loadings based on a survey, publicly available data, scientifically determined data, compiled user data, or any other source of data. In some instances, a movement monitoring module performs the above-described operations. In various embodiments, the movement monitoring module includes a metabolic loading module and a metabolic table module that determine the metabolic loading associated with the movement.

In one embodiment, a metabolic table is maintained based on the user information. The metabolic loadings in the metabolic table may be based on the user information. In some cases, the metabolic table is maintained based on a set of standard user information, in place of or in addition to user information from the user. The standard user information may include, for example, the average fitness characteristics of all individuals being the same age as the user, the same height as the user, etc. In another embodiment, instead of maintaining the metabolic table based on standard information, if the user has not provided user information, maintaining the metabolic table is delayed until the user information is obtained.

As illustrated in FIG. 10B, in one embodiment, the metabolic table is maintained as metabolic table 1050. Metabolic table 1050 may be stored in computing device 708 or apparatus 702, and may include information such as reference activity types (RATs) 1054, reference activity intensities (RAIs) 1052, and/or metabolic loadings (MLs) 1060. As illustrated in FIG. 10B, in one embodiment, RATs 1054 are arranged as rows 1058 in metabolic table 1050. Each of a set of rows 1058 corresponds to different RATs 1054, and each row 1058 is designated by a row index number. For example, the first RAT row 1058 may be indexed as RAT_0, the second as RAT_1, and so on for as many rows as metabolic table 1050 may include.

The reference activity types may include typical activities, such as running, walking, sleeping, swimming, bicycling, skiing, surfing, resting, working, and so on. The reference activity types may also include a catch-all category, for example, general exercise. The reference activity types may also include atypical activities, such as skydiving, SCUBA diving, and gymnastics. In one embodiment, a user defines a user-defined activity by programming computing device 708 (e.g., by an interface on electronic capsule 200) with information about the user-defined activity, such as pattern of movement, frequency of pattern, and intensity of movement. The typical reference activities may be provided, for example, by metabolic table 1050.

In one embodiment, reference activity intensities 1052 are arranged as columns in metabolic table 1050, and metabolic table 1050 includes columns 1056, each corresponding to different RAIs 1052. Each column 1056 is designated by a different column index number. For example, the first RAI column 1056 is indexed as RAI_0, the second as RAI_1, and so on for as many columns as metabolic table 1050 may include.

The reference activity intensities include, in one embodiment, a numeric scale. For example, the reference activity intensities may include numbers ranging from one to ten (representing increasing activity intensity). The reference activities may also be represented as a range of letters, colors, and the like. The reference activity intensities may be associated with the vigorousness of an activity. For example, the reference activity intensities may represented by ranges of heart rates or breathing rates.

In one embodiment, metabolic table 1050 includes metabolic loadings 1060. Each metabolic loading 1060 corresponds to a reference activity type 1058 of the reference activity types 1054 and a reference activity intensity 1056 of the reference activity intensities 1052. Each metabolic loading 1060 corresponds to a unique combination of reference activity type 1054 and reference activity intensity 1052. For example, in the column and row arrangement discussed above, one of the reference activity types 1054 of a series of rows 1058 of reference activity types, and one of the reference activity intensities 1052 of a series of columns 1056 of reference activity intensities correspond to a particular metabolic loading 1060. In such an arrangement, each metabolic loading 1060 may be identifiable by only one combination of reference activity type 1058 and reference activity intensity 1056.

This concept is illustrated in FIG. 10B. As shown, each metabolic loading 1060 is designated using a two-dimensional index, with the first index dimension corresponding to the row 1058 number and the second index dimension corresponding to the column 1056 number of the metabolic loading 1060. For example, in FIG. 10B, ML_2,3 has a first dimension index of 2 and a second dimension index of 3. ML_2,3 corresponds to the row 1058 for RAT_2 and the column 1056 for RAI_3. Any combination of RAT_M and RAI_N may identify a corresponding ML_M,N in metabolic table 1050, where M is any number corresponding to a row 1058 number in metabolic table 1050 and N is any number corresponding to a column 1056 number in metabolic table 1050. By way of example, the reference activity type RAT_3 may be "surfing," and the reference activity intensity RAI_3 may be "4." This combination in metabolic table 1050 corresponds to metabolic loading 1060 ML_3,3, which may, for example, represent 5.0 kcal/kg/hour (a typical value for surfing). In various embodiments, some of the above-described operations are performed by the movement monitoring module and some of the operations are performed by the metabolic table module.

Referring again to method 1000, in various embodiments, the movement is monitored by location tracking (e.g., Global Positioning Satellites (GPS), or a location-tracking device connected to a network via communication medium 704). The general location of the user, as well as specific movements of the user's body, are monitored. For example, the movement of the user's leg in x, y, and z directions may be monitored (e.g., by an accelerometer or gyroscope). In one embodiment, apparatus 702 receives an instruction regarding which body part is being monitored. For example, apparatus 702 may receive an instruction that the movement of a user's wrist, ankle, head, or torso is being monitored.

In various embodiments, the movement of the user is monitored and a pattern of the movement (pattern) is determined. For example, the pattern may be detected by an accelerometer or gyroscope. The pattern may be a repetition of a motion or a similar motion monitored by the method 1000; for example, the pattern may be geometric shape (e.g., a circle, line, oval) of repeated movement that is monitored. In some cases, the repetition of a motion in a geometric shape is not repeated consistently over time, but is maintained for a substantial proportion of the repetitions of movement. For instance, one occurrence of elliptical motion in a repetitive occurrence (or pattern) of ten circular motions may be monitored and determined to be a pattern of circular motion.

In further embodiments, the geometric shape of the pattern of movement is a three dimensional (3D) shape. To illustrate, the pattern associated with the wrist of a person swimming the butterfly stroke may be monitored and analyzed into a geometric shape in three dimensions. The pattern may be complicated, but it may be described in a form can be recognized by method 1000. Such a form may include computer code that describes the spatial relationship of a set of points, along with changes in acceleration forces that are experienced along those points as, for example, a sensor travels throughout the pattern.

In various embodiments, monitoring the pattern includes monitoring the frequency with which the pattern is repeated (or pattern frequency). The pattern frequency may be derived from a repetition period of the pattern (or pattern repetition period). The pattern repetition period may be the length of time elapsing from when a device or sensor passes through a certain point in a pattern and when the device or sensor returns to that point when the pattern is repeated. For example, the sensor may be at point x, y, z at time t_0. The device may then move along the trajectory of the pattern, eventually returning to point x, y, z at time_1. The pattern repetition period would be the difference between t_1 and t_0 (e.g., measured in seconds). The pattern frequency may be the reciprocal of the pattern repetition period, and may have units of cycles per second. When the pattern repetition period is, for example, two seconds, the pattern frequency would be 0.5 cycles per second.

In some embodiments, various other inputs are used to determine the activity type and activity intensity. For example, monitoring the movement may include monitoring the velocity at which the user is moving (or the user velocity). The user velocity may, for example, have units of kilometers per hour. In one embodiment, the user's location information is monitored to determine user velocity. This may be done by GPS, through communication medium 704, and so on. The user velocity may be distinguished from the speed of the pattern (or pattern speed). For example, the user may be running at a user velocity of 10 km/hour, but the pattern speed of the user's wrist may be 20 km/hour at a given point (e.g., as the wrist moves from behind the user to in front of the user). The pattern speed may be monitored using, for example, an accelerometer or gyroscope.

In one embodiment, the user's altitude is monitored. This may be done, for example, using an altimeter, user location information, information entered by the user, etc. In another embodiment, the impact the user has with an object (e.g., the impact of the user's feet with ground) is monitored. This may be done using an accelerometer or gyroscope. In some cases, the ambient temperature is measured (e.g., by apparatus 702). Apparatus 702 may associate a group of reference activity types with bands of ambient temperature. For example, when the ambient temperature is zero degrees Celsius, activities such as skiing, sledding, and ice climbing are appropriate selections for reference activity types, whereas surfing, swimming, and beach volleyball may be inappropriate. The ambient humidity may also be measured (e.g., by a hygrometer). In some cases, pattern duration (i.e., the length of time for which particular movement pattern is sustained) is measured.

In one embodiment, monitoring the movement is accomplished using sensors configured to be attached to a user's body. Such sensors may include a gyroscope or accelerometer to detect movement, and a heart-rate sensor, each of which may be embedded in a wristband that a user can wear on the user's wrist or ankle, such as wristband 100. Additionally, various modules and sensors that may be used to perform the above-described operations may be embedded in electronic capsule 200. In various embodiments, the above-described operations are performed by the movement monitoring module.

Method 1000, in one embodiment, involves determining the user activity type from the set of reference activity types. Once detected, the pattern may be used to determine the user activity type from a set of reference activity types. Each reference activity type is associated with a reference activity type pattern. The user activity type may be determined to be the reference activity type that has a reference activity type pattern that matches the pattern measured by method 1000.

In some cases, the pattern that matches the reference activity type pattern will not be an exact match, but will be substantially similar. In other cases, the patterns will not even be substantially similar, but it may be determined that the patterns match because they are the most similar of any patterns available. For example, the reference activity type may be determined such that the difference between the pattern of movement corresponding to this reference activity type and the pattern of movement is less than a predetermined range or ratio. In one embodiment, the pattern is looked up (for a match) in a reference activity type library. The reference activity type library may be included in the metabolic table. For example, the reference type library may include rows in a table such as the RAT rows 1058.

In further embodiments, method 1000 involves using the pattern frequency to determine the user activity type from the set of reference activity types. Several reference activity types, however, may be associated with similar patterns (e.g., because the wrist moves in a similar pattern when running versus walking). In such cases, the pattern frequency is used to determine the activity type (e.g., because the pattern frequency for running is higher than the pattern frequency for walking).

Method 1000, in some instances, involves using additional information to determine the activity type of the user. For example, the pattern for walking may be similar to the pattern for running. The reference activity of running may be associated with higher user velocities and the reference activity of walking with lower user velocities. In this way, the velocity measured may be used to distinguish two reference activity types having similar patterns.

In other embodiments, method 1000 involves monitoring the impact the user has with the ground and determining that, because the impact is larger, the activity type, for example, is running rather than walking. If there is no impact, the activity type may be determined to be cycling (or other activity where there is no impact). In some cases, the humidity is measured to determine whether the activity is a water sport (i.e., whether the activity is being performed in the water). The reference activity types may be narrowed to those that are performed in the water, from which narrowed set of reference activity types the user activity type may be determined. In other cases, the temperature measured is used to determine the activity type.

Method 1000 may entail instructing the user to confirm the user activity type. In one embodiment, a user interface is provided such that the user can confirm whether a displayed user activity type is correct, or select the user activity type from a group of activity types.

In further embodiments, a statistical likelihood for of choices for user activity type is determined. The possible user activity types are then provided to the user in such a sequence that the most likely user activity type is listed first (and then in descending order of likelihood). For example, it may be determined that, based on the pattern, the pattern frequency, the temperature, and so on, that there is an 80% chance the user activity type is running, a 15% chance the user activity type is walking, and a 5% chance the user activity is dancing. Via a user interface, a list of these possible user activities may be provided such that the user may select the activity type the user is performing. In various embodiments, some of the above-described operations are performed by the metabolic loading module.

Method 1000, in some embodiments, also includes determining the user activity intensity from a set of reference activity intensities. The user activity intensity may be determined in a variety of ways. For example, the repetition period (or pattern frequency) and user activity type (UAT) may be associated with a reference activity intensity library to determine the user activity intensity that corresponds to a reference activity intensity. FIG. 10C illustrates one embodiment whereby this aspect of method 1000 is accomplished, including reference activity intensity library 1080. Reference activity intensity library 1080 is organized by rows 1088 of reference activity types 1084 and columns 1086 of pattern frequencies 1082. In FIG. 10C, reference activity library 1080 is implemented in a table. Reference activity library 1080 may, however, be implemented other ways.

In one embodiment, it is determined that, for user activity type 1084 UAT_0 performed at pattern frequency 1082 F_0, the reference activity intensity 1090 is RAI_0,0. For example, UAT 1084 may correspond to the reference activity type for running, a pattern frequency 1082 of 0.5 cycles per second for the user activity type may be determined. Reference activity intensity library 1080 may determine that the UAT 1084 of running at a pattern frequency 1082 of 0.5 cycles per second corresponds to an RAI 1090 of five on a scale of ten. In another embodiment, the reference activity intensity 1090 is independent of the activity type. For example, the repetition period may be five seconds, and this may correspond to an intensity level of two on a scale of ten.

Reference activity intensity library 1080, in one embodiment, is included in metabolic table 1050. In some cases, the measured repetition period (or pattern frequency) does not correspond exactly to a repetition period for a reference activity intensity in metabolic table 1050. In such cases, the correspondence may be a best-match fit, or may be a fit within a tolerance. Such a tolerance may be defined by the user or by a system administrator, for example.

In various embodiments, method 1000 involves supplementing the measurement of pattern frequency to help determine the user activity intensity from the reference activity intensities. For example, if the user activity type is skiing, it may be difficult to determine the user activity intensity because the pattern frequency may be erratic or otherwise immeasurable. In such an example, the user velocity, the user's heart rate, and other indicators (e.g., breathing rate) may be monitored to determine how hard the user is working during the activity. For example, higher heart rate may indicate higher user activity intensity. In a further embodiment, the reference activity intensity is associated with a pattern speed (i.e., the speed or velocity at which the sensor is progressing through the pattern). A higher pattern speed may correspond to a higher user activity intensity.

Method 1000, in one embodiment, determines the user activity type and the user activity intensity by using sensors configured to be attached to the user's body. Such sensors may include, for example, a gyroscope or accelerometer to detect movement, and a heart-rate sensor, each of which may be embedded in a wristband that a user can wear on the user's wrist or ankle, such as wristband 100. Additionally, various sensors and modules that may be used to preform above-described operations of method 1000 may be embedded in electronic capsule 200 or other hardware. In various embodiments, the above-described operations are performed by the movement monitoring module.

Referring again to FIG. 10A, method 1000 includes creating and updating a metabolic activity score based on the movement and the user information. Method 1000 may also include determining a metabolic loading associated with the user and the movement. In one embodiment, a duration of the activity type at a particular activity intensity (e.g., in seconds, minutes, or hours) is determined. The metabolic activity score may be created and updated by, for example, multiplying the metabolic loading by the duration of the user activity type at a particular user activity intensity. If the user activity intensity changes, the new metabolic loading (associated with the new user activity intensity) may be multiplied by the duration of the user activity type at the new user activity intensity. In one embodiment, the activity score is represented as a numerical value. By way of example, the metabolic activity score may be updated by continually supplementing the metabolic activity score as new activities are undertaken by the user. In this way, the metabolic activity score continually increases as the user participates in more and more activities.

In one embodiment, the metabolic activity score is based on score periods. Monitoring the movement may include determining, during a score period, the metabolic loading associated with the movement. Score periods may include segments of time. The user activity type, user activity intensity, and the corresponding metabolic loading, in one embodiment, are measured (or determined) during each score period, and the metabolic activity score may be calculated for that score period. As the movement changes over time, the varying characteristics of the movement are captured by the score periods.

Method 1000 includes, in one embodiment, creating and updating a set of periodic activity scores. Each period activity score is based on the movement monitored during a set of score periods, and each period activity score is associated with a particular score period of the set of score periods. In one example, the metabolic activity score is created and updated as an aggregate of period activity scores, and the metabolic activity score may represent a running sum total of the period activity scores.

In one embodiment, method 1000 includes applying a score period multiplier to the score period to create an adjusted period activity score. The metabolic activity score in such an example is an aggregation of adjusted period activity scores. Score period multipliers may be associated with certain score periods, such that the certain score periods contribute more or less to the metabolic activity score than other score periods during which the same movement is monitored. For example, if the user is performing a sustained activity, a score period multiplier may be applied to the score periods that occur during the sustained activity. By contrast, a multiplier may not be applied to score periods that are part of intermittent, rather than sustained, activity. As a result of the score period multiplier, the user's sustained activity may contribute more to the metabolic activity score than the user's intermittent activity. The score period multiplier may allow consideration of the increased demand of sustained, continuous activity relative to intermittent activity.

The score period multiplier, in one instance, is directly proportional to the number of continuous score periods over which a type and intensity of the movement is maintained.

The adjusted period activity score may be greater than or less than the period activity score, depending on the score period multiplier. For example, for intermittent activity, the score period multiplier may be less than 1.0, whereas for continuous, sustained activity, the score period multiplier may be greater than 1.0.

In one embodiment, method 1000 entails decreasing the metabolic activity score when the user consumes calories. For example, if the user goes running and generates a metabolic activity score of 1,000 as a result, but then the user consumes calories, the metabolic activity score may be decreased by 200 points, or any number of points. The decrease in the number of points may be proportional to the number of calories consumed. In other embodiments, information about specific aspects of the user's diet is obtained, and metabolic activity score points are awarded for healthy eating (e.g., fiber) and subtracted for unhealthy eating (e.g., excessive fat consumption).

The user, in one embodiment, is pushed to work harder, or not as hard, depending on the user lifestyle. This may be done, for example, by adjusting the metabolic loadings based on the user lifestyle. To illustrate, a user with a highly active lifestyle may be associated with metabolic loadings that result in a lower metabolic activity score when compared to a user with a less active lifestyle performing the same movements. This results in requiring the more active user to, for example, work (or perform movement) at a higher activity intensity or for a longer duration to achieve the same metabolic activity score as the less active user participating in the same activity type (or movements).

In one embodiment, the metabolic activity score is reset every twenty-four hours. The metabolic activity score may be continually incremented and decremented throughout a measuring period, but may be reset to a value (e.g., zero) at the end of twenty-four hours. The metabolic activity score may be reset after any given length of time (or measuring period)—for example, the activity score may be continually updated over the period of one week, or one month.

In one embodiment, because the metabolic activity score was greater than a certain amount for the measuring period, the metabolic activity score is reset to a number greater than zero. As such, the user effectively receives a credit for a particularly active day, allowing the user to be less active the next day without receiving a lower metabolic activity score for the next day. In a further embodiment, because the metabolic activity score was less than a predetermined value for the measuring period, the metabolic activity score is reset to a value less than zero. The user effectively receives a penalty for that day, and would have to make up for a particularly inactive or overly consumptive day by increasing the user's activity levels the next day. In various embodiments, creating and updating the metabolic activity score is performed by a movement monitoring module or by a metabolic activity score module.

Referring again to FIG. 10A, operation 1006 involves detecting a fatigue level. In one embodiment, the fatigue level is the fatigue level of the user. The fatigue level, in one embodiment, is a function of recovery. The fatigue level may be detected in various ways. In one example, the fatigue level is detected by measuring a heart rate variability (HRV) of a user using logic circuits 240 (discussed above in reference in to FIG. 1) and is based at least in part on the recovery measured. Further, representations of fatigue level are described above (e.g., numerical, descriptive, etc.). When the HRV is more consistent (i.e., steady, consistent amount of time between heartbeats), for example, the fatigue level may be higher. In other words, the body is less fresh and well-rested. When HRV is more sporadic (i.e., amount of time between heartbeats varies largely), the fatigue level may be higher.

At operation 1006, HRV may be measured in a number of ways (discussed above in reference in to FIG. 1). Measuring HRV, in one embodiment, involves the combination of wrist biosensor 210 and finger biosensor 220. Wrist biosensor 210 may measure the heartbeat in the wrist of one arm while finger sensor 220 measures the heartbeat in a finger of the hand of the other arm. This combination allows the sensors, which in one embodiment are conductive, to measure an electrical potential through the body. Information about the electrical potential provides cardiac information (e.g., HRV, fatigue level, heart rate information, and so on), and such information is processed at operation 1006. In other embodiments, the HRV is measured using sensors that monitor other parts of the user's body, rather than the finger and wrist. For example, the sensors may monitor the ankle, leg, arm, or torso. In some instances, the HRV is measured by a module that is not attached to the body, but is a standalone module.

In one embodiment, at operation 1006, the fatigue level is detected based solely on the HRV measured. The fatigue level, however, may be based on other measurements (e.g., measurements monitored by method 1000). For example, the fatigue level may be based on the amount of sleep that is measured for the previous night, the duration and type of user activity, and the intensity of the activity determined for a previous time period (e.g., exercise activity level in the last twenty-four hours). By way of example, these factors may include stress-related activities such as work and driving in traffic, which may generally cause a user to become fatigued. In some cases, the fatigue level is detected by comparing the HRV measured to a reference HRV. This reference HRV may be based on information gathered from a large number of people from the general public. In another embodiment, the reference HRV is based on past measurements of the user's HRV.

At operation 1006, in one embodiment, the fatigue level is detected once every twenty-four hours. This provides information about the user's fatigue level each day so that the user's activity levels may be directed according to the fatigue level. In various embodiments, the fatigue level is detected more or less often. Using the fatigue level, a user may determine whether or not an activity is necessary (or desirable), the appropriate activity intensity, and the appropriate activity duration. For example, in deciding whether to go on a run, or how long to run, the user may want to use operation 1006 to assess the user's current fatigue level. Then, the user may, for example, run for a shorter time if the user is more fatigued, or for a longer time if the user is less fatigued. In some cases, it may be beneficial to detect the fatigue level in the morning, upon the user's waking up. This may provide the user a reference for how the day's activities should proceed.

Referring again to FIG. 10A, operation 1008 involves creating and updating a dynamic recovery profile based on an archive. The archive includes historical information about the fatigue level (which is described above with reference to operation 1006). In one embodiment, the archive includes historical information about the movement and the metabolic activity score. The archive may include, for example, information about past user activity types, past user activity intensities, and past fatigue levels, as well as the relationships between each of these (e.g., if fatigue levels are particularly high after a certain user activity type or after a user achieve a particular metabolic activity score). The archive may also include historical information relative to particular score periods and score period multipliers. The archive, in various embodiment, is embedded in apparatus 702 or computing device 708.

The dynamic recovery profile is created and updated based on the archive. In one embodiment, being based on the user's actual (historical) and detected fatigue level, the dynamic recovery profile is specific to the user's personal fatigue characteristics and responses. The dynamic recovery profile, for example, may reflect information indicating that the user typically has a very high fatigue level when the user gets less than six hours of sleep. In another instance, the dynamic recovery profile may indicate that the user typically has a very high fatigue level following a day in which the user achieves a metabolic activity score above a certain amount (or a particular user activity intensity that is sustained over a particular amount of time). In another example, the user's fatigue levels may not follow typical trends, and the archive can account for this. For example, while the average user may present a fatigue level of 4 when well rested, the archive may reflect that the user has recorded a fatigue level of 6 when rested. The archive provides a means for the fatigue level measurement to be normalized to the user's specific HRV and fatigue levels.

The dynamic recovery profile, in other words, learns the fatigue tendencies of the user by compiling, by way of the archive, data about the user. Moreover, the dynamic recovery profile provides a contoured baseline that is continually adjusted as the user's performance, fatigue, and recovery tendencies change over time. In one embodiment, the dynamic recovery profile represents a range of fatigue levels that are normal for the user. For example, based on data in the archive, the dynamic recovery profile may indicate that fatigue levels between 40 and 60 are typical for the user. The dynamic recovery profile, in one embodiment, accounts for changes in the historical information over time by updating the dynamic recovery profile on a periodic basis. In a further embodiment, the user programs the dynamic recovery profile to refresh periodically to capture recent historical information. Updates to the dynamic recovery profile, in one instance, are based on rates or amounts of change that may occur over time to the historical information in the archive.

The dynamic recovery profile, in one embodiment, is implemented in conjunction with an archive table that represents data and relationships of parameters relative to that data. In one instance, the archive table uses the parameters of metabolic activity score (MAS), date, fatigue level, sleep time, and average user activity intensity (UAI) to organize the data and extract relational information. This is illustrated in FIG. 10D, which provides archive table 1020 (which may be embodied in the archive). Archive table 1020 includes the parameters of date 1022, MAS 1024, average UAI 1026, sleep time 1028, and fatigue level 1030. In other instances, archive table 1020 may include only information about the user's measured fatigue levels.

In various embodiments, archive table 1020 includes any other parameters that are monitored, determined, or created by method 1000. In some embodiments, archive table 1020 includes analytics. Such analytics include statistical relationships of the various parameters in archive table 1020. For example, archive 1020 may include analytics such as mean ratio of fatigue level to MAS, mean ratio of sleep to MAS, mean fatigue level by day of the week, and so on. These analytics allow the dynamic recovery profile to back into optimal performance regimens specific to the user.

To illustrate, the dynamic recovery profile may determine (from archive table 1020) that the user has a mean fatigue level of 7 following a day when sleep to MAS ratio is 6 to 2,000, and may determine that the user typically achieves a below average MAS on days when the fatigue level is 7 or higher. In such an example, the dynamic recovery profile may indicate that the user should get more sleep, or should strive for a lower MAS, to avoid becoming overly fatigued. The dynamic recovery profile, in one embodiment, reflects information about the user's optimal fatigue scenarios; that is, fatigue levels at which the user tends to historically achieve a high MAS. The optimal fatigue scenario may be specific to the user (e.g., some users may have greater capacity for activity when more fatigued, etc.).

Referring again to FIG. 10A, operation 1010 involves creating and updating an interpreted recovery score based on the fatigue level and the dynamic recovery profile. The interpreted recovery score, because it is based on both the fatigue level detected and on actual, historical results (as incorporated into the dynamic recovery profile), provides higher resolution and additional perspective into the user's current performance state. In one embodiment, the interpreted recovery score supplements the fatigue level with information to account for the user's past activities (e.g., from the archive). The interpreted recovery score may be, for example, a number selected from a range of numbers. In one case, the interpreted recovery score may be proportional to the fatigue level (e.g., higher fatigue corresponds to higher interpreted recovery score). In one embodiment, a typical interpreted recovery score ranges from 40 to 60.

The interpreted recovery score, by way of the dynamic recovery profile (which is based on the archive), in one embodiment, has available information about the user activity type, the user activity intensity, and the duration of the user's recent activities, as well as analytics of historical information pertaining to the user's activities. The interpreted recovery score may use this information, in addition to the current fatigue level, to provide higher resolution into the user's capacity for activity. For example, if the user slept poorly, but for some reason this lack of sleep is not captured in the fatigue level measurement (e.g., if the HRV is consistent rather than sporadic), the interpreted recovery score may be adjusted to account for the user's lack of sleep. In this example, the lack of sleep information would be available via archived activity type detection and movement monitoring. In other embodiments, the interpreted recovery score will be based only on historic fatigue levels specific to the user. In various embodiments, operation 1010 is performed by interpreted recovery score module 808.

Figure 11:
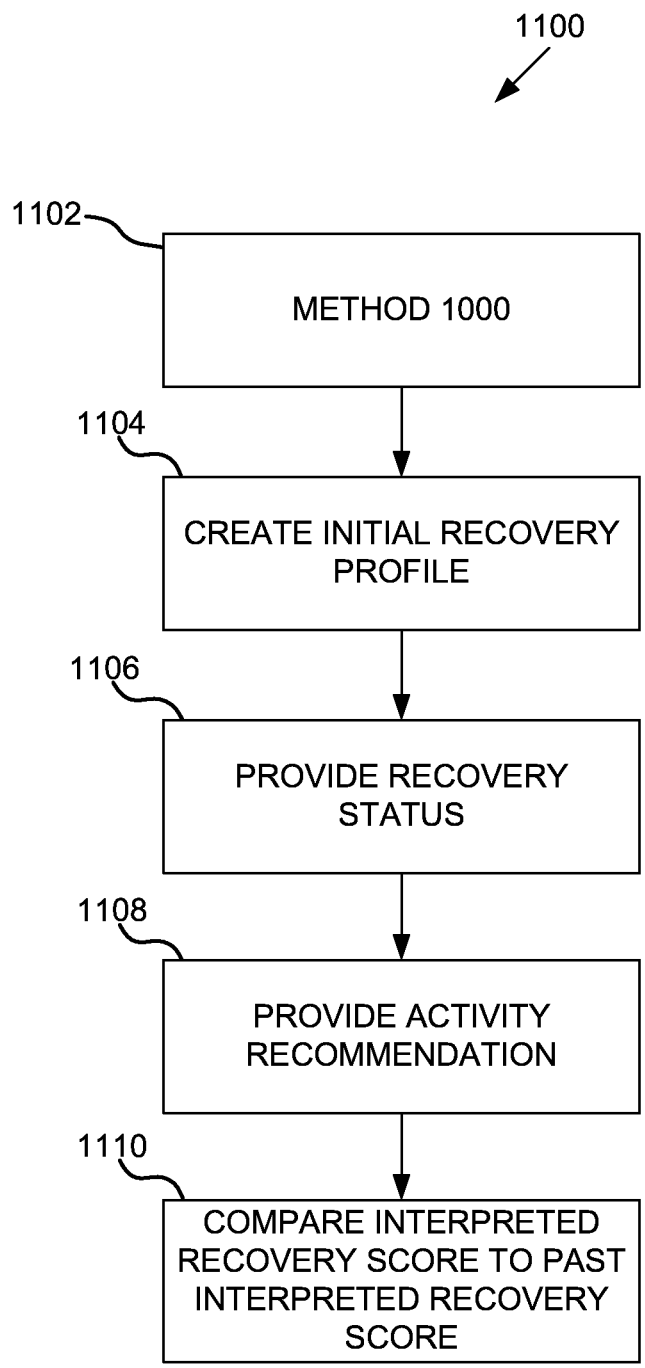
FIG. 11 is an operational flow diagram illustrating an example of a method for providing an interpreted recovery score including providing a recovery status.

FIG. 11 is an operational flow diagram illustrating an example method 1100 for providing an interpreted recovery score in accordance with an embodiment of the present disclosure. In one embodiment, apparatus 702, wristband 100, and electronic capsule 200 perform various operations of method 1100. In addition, method 1100 may include, at operation 1102, various operations from method 1000.

In one embodiment, at operation 1104, method 1100 involves creating an initial recovery profile. The initial recovery profile is based on a comparison of the user information to normative group information. The normative group may include information collected from a group of people other than the user. The normative group information may be averaged and used as a baseline for the initial recovery profile (an expectation of user activity levels) before any historical information is generated.

The normative group information, in one embodiment, is adjusted according to different possible sets of user information. For example, the normative group information may collected and average (or otherwise statistically analyzed). A user information multiplier may be created based on a comparison of the normative group information and the user information. The user information multiplier may be applied to the normative group information to adjust the normative group information such that the normative group information becomes specific to the user's information and characteristics. For example, an average value of the normative group information may be increased if the user is younger than the average group member, or may decrease the average for a user that is less active than the average group member. This adjustment, in one embodiment, results in an initial recovery profile that is based on the normative group information but is specific to the user information (and the user). The initial recovery profile may represent a user-specific expectation for activity level (e.g., for MAS). The initial recovery profile may also represent a user-specific expectation for fatigue level. In various embodiments, operation 1104 is performed by initial recovery profile module 902.

In one embodiment, creating and updating the dynamic recovery profile is further based on the initial recovery profile. In such an embodiment, if the historical information about the user's fatigue levels indicates that the user is typically more fatigued than the user's initial recovery profile indicates the user is expected to be, the dynamic recovery profile is updated in a way that reflects this discrepancy. For example, based on actual fatigue levels detected, the dynamic recovery profile may expect a higher fatigue level than indicated by the initial recovery profile.

The dynamic recovery profile, in one embodiment, learns over time what fatigue levels or range of fatigue level is normal from the user. During this learning phase, the dynamic recovery profile may include a blend of information from the archive and the initial recovery profile. The dynamic recovery profile, in such an embodiment, more heavily weights the information from the archive as the archive gathers information that is increasingly complete. For example, before taking any fatigue measurements, the dynamic recovery profile may be based entirely on the initial recovery profile (which is derived from normative data). Then, for example, after detecting and storing in the archive two weeks' worth of fatigue level information from the user the dynamic recovery profile may weigh the information from the archive more heavily (e.g., base the dynamic recovery profile 50% on the archive and 50% on the initial recovery profile). Eventually, once the dynamic recovery profile captures complete information in the archive (e.g., after two months' worth of detecting fatigue level information), the dynamic recovery profile may phase out the initial recovery profile entirely. That is, the dynamic recovery profile may be entirely based on the archive. In other words, the dynamic recovery profile, in such an embodiment, phases out the initial recovery profile as the amount of information in the archive increases.

In further embodiments, the historical information about the user activity type or user activity intensity (or MAS) may differ from the initial recovery profile in a way that warrants a shift in expected activity levels. For example, the initial recovery profile may expect a higher or lower amount of user activity intensity (or MAS) than is in reality measured. This discrepancy may be resolved by updating the dynamic recovery profile based on the archive. For example, the dynamic recovery profile may be decreased because the user is not performing at the level (e.g., MAS) initially expected (or indicated by the initial recovery profile).

In addition, the user information may change in a way that causes the initial recovery profile, created at operation 1104, to lose its accuracy. The dynamic recovery profile may be updated to reflect such changes, such that the dynamic recovery profile is more accurate. For example, the user's weight or age may change. As a result, the normative group data used to generate the initial recovery profile may become stale. This may be resolved by updating the dynamic recovery profile (e.g., with the user's actual weight). The dynamic recovery profile may function as a version of the initial recovery profile adjusted according to the historical information in the archive.

Referring again to FIG. 11, in one embodiment, method 1100 includes operation 1106, which involves providing a recovery status based on the interpreted recovery score. The recovery status may be based on various thresholds of the interpreted recovery score. For example, the recovery status may be represented on a numerical, descriptive, or color scale, or the like. In one instance, the recovery status is directly proportional to the interpreted recovery score. The recovery status, in such an example, may indicate the user's need to rest from strenuous activity or high levels of activity. In the case that the recovery status is numerical, a negative recovery status may indicate that the user is over-rested, a positive recovery status may indicate that rest is needed, and a small recovery status (i.e., near-zero) may indicate an optimal recovery level.

In one embodiment of the descriptive recovery status, the recovery status includes the following: fatigued, recovered, and optimal. If the interpreted recovery score is below a lowest threshold, in the descriptive recovery status example, the recovery status will be "recovered." This indicates that the user is fully rested. In some instances, "recovered" is distinguished from "optimal" because "recovered" indicates that the user is too rested and has less capacity for activity. Further illustrating the descriptive recovery status example, if the interpreted recovery score is above the lowest threshold but below the highest threshold, the recovery status will be "optimal." This indicates that the user has peak capacity for activity. "Optimal" recovery status may be associated with the scenario in which the user is rested, but no overly so. If the interpreted recovery score is above the highest threshold, the recovery status (in this example) will be "fatigued." This indicates that the user has minimal capacity for activity because the user needs to rest. In various embodiments, the recovery status is based on any number of thresholds and may be further stratified for higher granularity into the user's recovery status.

Method 1100, in one embodiment, includes operation 1108, as illustrated in FIG. 11. Operation 1108 involves providing an activity recommendation based on the interpreted recovery score. For example, if the interpreted recovery score is high, indicating that the user is more fatigued, lower user activity intensities may be recommended. If the interpreted recovery score is low, indicating that the user is well-rested, higher activity intensities may be recommended. This example applies to recommended activity durations in a similar fashion (e.g., longer durations if less fatigued, etc.).

In a further embodiment, method 1100 includes operation 1110, which involves comparing the interpreted recovery score to a past interpreted recovery score. In this embodiment, the interpreted recovery is associated with a measuring period and the past interpreted recovery score is associated with a past measuring period. Interpreted recovery scores may be stored and associated with past measuring periods (i.e., the measured period during which the interpreted recovery score was created). In this way, past interpreted recovery scores and information associated therewith may be used to inform the user's current activity.

At operation 1110, comparing the scores the may include providing a simple numerical readout of both scores (e.g., side by side). In one embodiment, information about the time of day associated with the past interpreted recovery score is presented. For example, the time of day at which the past interpreted recovery score was created may be presented. This may inform the user of how the user's current interpreted activity score relates to the past interpreted recovery score, allowing the user to gauge how the interpreted recovery score may correlate to the user's physical state or feeling.

In another embodiment, the past interpreted recovery score is displayed on a graph (e.g., a line or bar graph) as a function of time (e.g., comparing against other past interpreted recovery scores from past measuring periods). The graph may be overlaid with a graph of the current interpreted recovery score. One of ordinary skill in the art will appreciate other ways to compare the interpreted recovery scores. In various embodiments, operation 1110 is performed by interpreted recovery score module 808.

Figure 12:
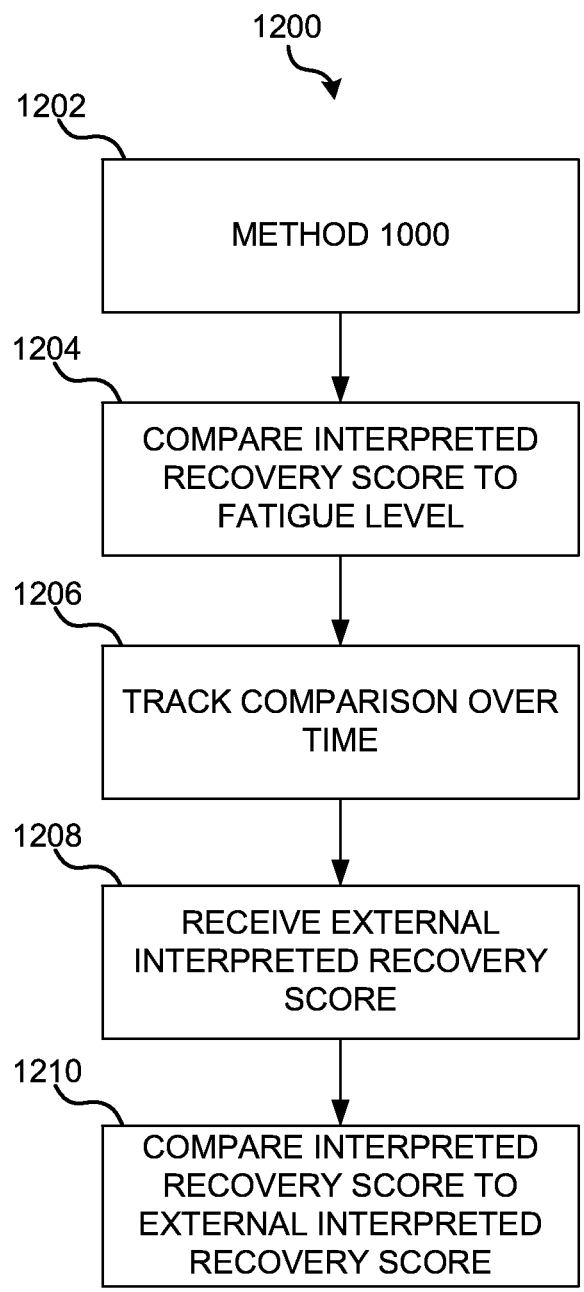
FIG. 12 is an operational flow diagram illustrating an example of a method for providing an interpreted recovery score including comparing the interpreted recovery score to an external interpreted recovery score.

FIG. 12 is an operational flow diagram illustrating an example method 1200 for providing an interpreted recovery score in accordance with an embodiment of the present disclosure. In one embodiment, apparatus 702, wristband 100, and electronic capsule 200 perform various operations of method 1200.

In one embodiment, at operation 1204, method 1200 involves performing a comparison of the interpreted recovery score to the fatigue level. Operation 1206, in another embodiment, involves tracking the comparison over time. As described above, the fatigue level may be associated with physical phenomena, including HRV, while the interpreted recovery score is based on actual, historical information (via the dynamic recovery profile), include past fatigue levels for the user. In one embodiment, tracking the comparison over time (operation 1206) provides insight into how lifestyle choices affect performance capacity and fatigue levels. For example, the comparison may provide a normalization for the user's typical fatigue levels as they change over time relative to past fatigue levels.

Referring again to FIG. 12, in one embodiment, at operation 1208, method 1200 involves receiving an external interpreted recovery score. The external interpreted recovery score may be received in a number of ways (e.g., via communication medium 704). The external interpreted recovery score may be created and updated in a manner similar to the creating and updating of the interpreted recovery (operation 1010). The external interpreted recovery score may be from a second user, who is any user other than the user. The second user may be a friend or associate of the first user. In various embodiments, operation 1208 is performed by interpreted recovery score module 808.

At operation 1210, an embodiment of method 1200 involves comparing the external interpreted recovery score to the interpreted recovery score. The external interpreted recovery score may be compared to the interpreted recovery score in a fashion substantially similar to the comparison performed in operation 1110. Operation 1210 allows the user to compare the user's interpreted recovery score (based on the user's fatigue level) to the interpreted recovery score of another user (based on the other user's fatigue level). In various embodiments, operation 1210 is performed by interpreted recovery score module 808.

Referring back to method 1000 one or more operations may be further leveraged to provide additional information to a user. For example, various embodiments of the present disclosure may identify when a user is progressing through a "fitness cycle." As utilized herein, the term fitness cycle may refer to a period that spans experiencing some type of physical load, e.g., a workout, through recovery. That is, HRV can be determined and leveraged (in the context of learned user characteristics/recovery profile described above) in such a way as to identify and present fitness cycle information to a user.

Figure 13A:
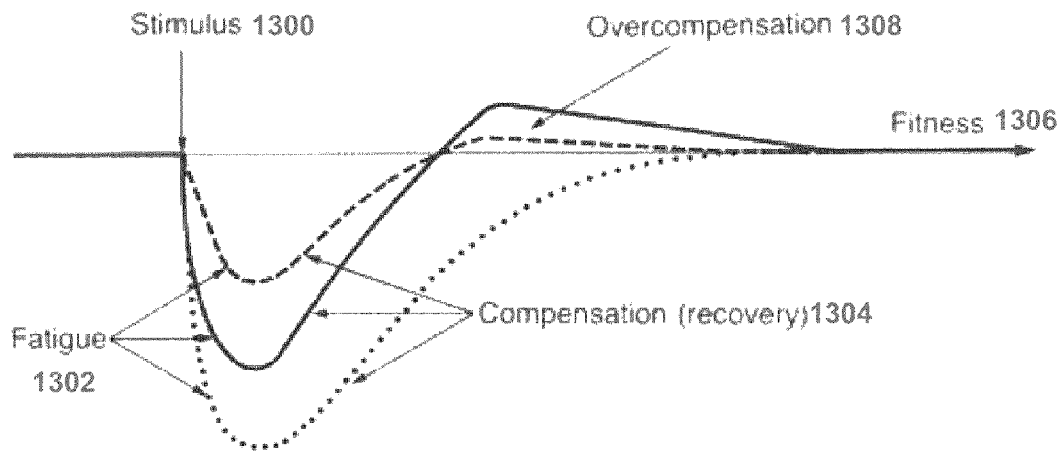
FIG. 13A is an example graphical representation of fitness cycles.
Figure 13B:
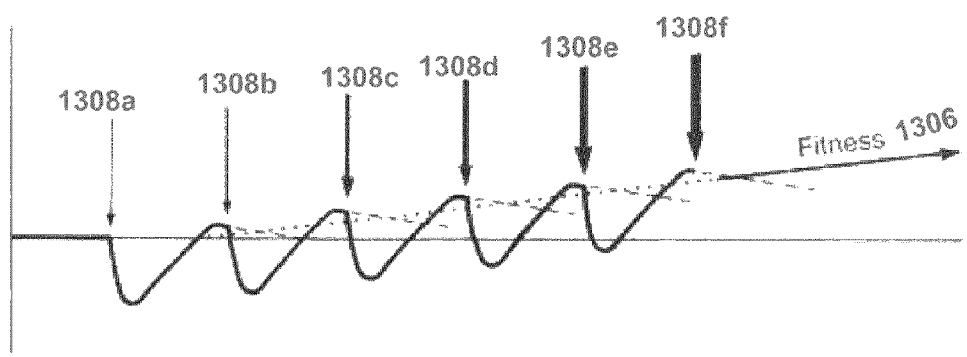
FIG. 13B is an example graphical representation of a plurality of fitness cycles over time.

That is, fitness gains are generally made when the human body fully recovers from an activity, such as a workout. FIGS. 13A and 13B are graphs representing example fitness cycle information/data that may be obtained and/or presented to a user in accordance with one embodiment. In particular, FIG. 13A illustrates example fitness cycles. A stimulus or load 1300 may be experienced by the human body during a workout, where the fitness level of the human body, i.e. the ability to perform work at a given rate, decreases as the workout progresses. In other words, the human body becomes fatigued. As illustrated in FIG. 13A, different levels of fatigue 1302 can be experienced depending whether, e.g., a training session was adequate (solid line), too easy (hashed line), or too hard (dotted line). After the end of the workout, which would correspond with the greatest level of fatigue experienced, the human body can begin to rebuild itself (e.g., rebuild muscle fibers and nervous system) to return to its original baseline fitness level 1306. The period from this state of post-workout fatigue back to the original baseline fitness level 1306 may be referred to as compensation or recovery 1304. It should be noted that recovery can be considered a function of fatigue (or vice-versa), where for example, as the human body becomes less fatigued, from, e.g., rest, the human body can be considered to be undergoing recovery.

If the human body is allowed to properly recover between an initial instance of fatigue and a subsequent activity, such as another workout, the human body can experience a phenomenon referred to as overcompensation 1308, which can be a continuation of the recovery process. Overcompensation can occur when the human body (e.g., muscle fibers and nervous system) is built up beyond the original baseline fitness level 1306, creating a new fitness level that surpasses the original baseline fitness level.

FIG. 13B illustrates an example graphical representation of fitness level 1306 over time. If overcompensation occurs subsequent to each workout (as indicated by arrows 1308a-1308f), over time, the human body can experience increased baseline fitness levels 1306 and/or can increased capability for athletic performance.

However, if the human body engages in stimuli or loading, such as subsequent workouts, before proper recovery can occur, or if the resulting fatigue level is too severe, overcompensation can fail to occur, and athletic performance and fitness may either remain stagnant or in some instances, may even degrade. Additionally still, workouts that are too easy and/or engaging in recovery that lasts too long may also result in static fitness levels. Accordingly, a user presented with information regarding when the user is progressing through fitness cycles can determine whether or not they are engaging in activity and recovery that is improving their fitness in a quantifiable manner, and thereby allowing for adjustment(s) to their activity and recovery. It should be noted that stress (as previously discussed) may be considered to be a stimulus from which fatigue can result.

Figure 14:
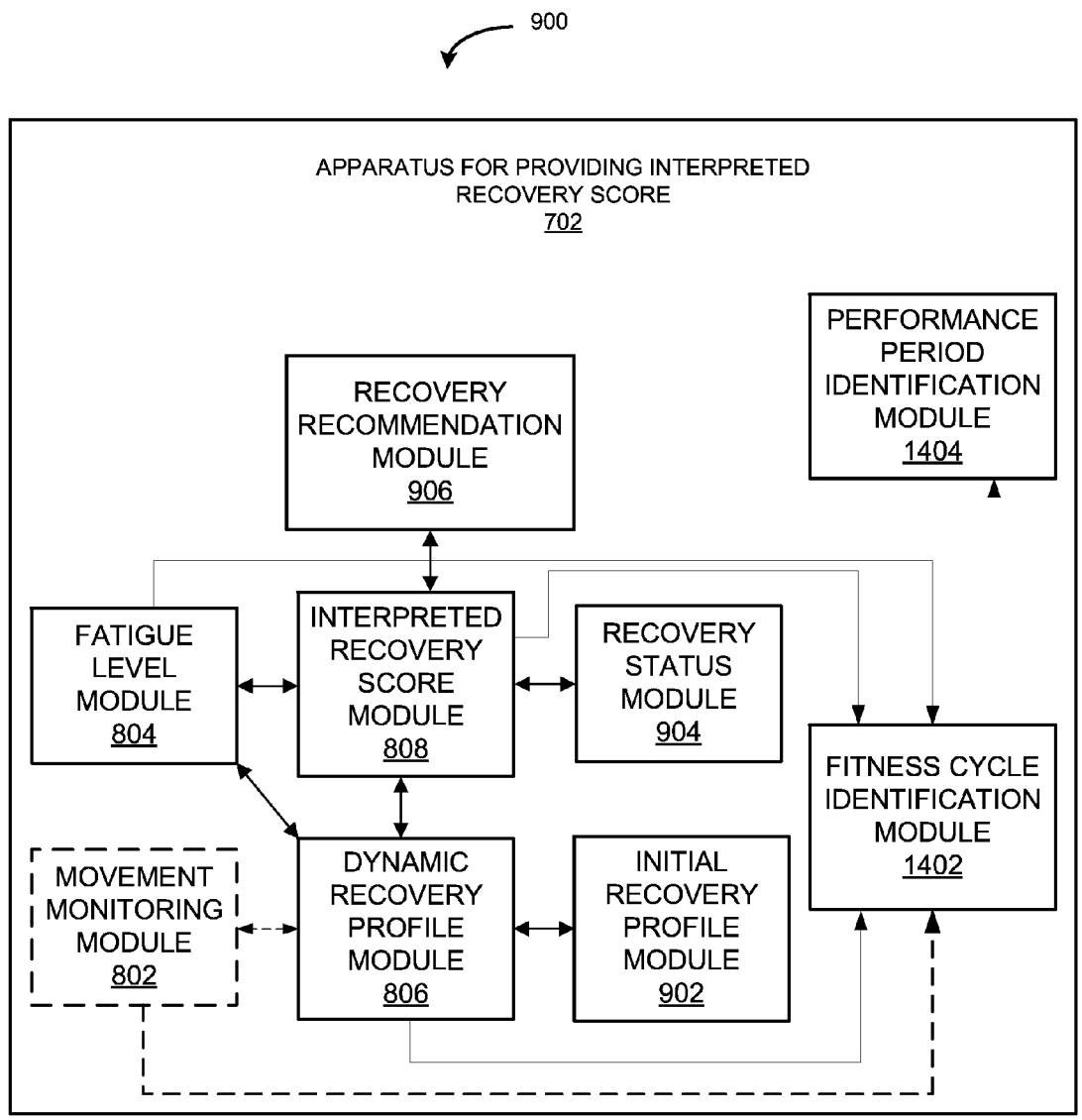
FIG. 14 illustrates the example apparatus for providing an interpreted recovery score of FIG. 9 utilized as a platform for identifying performance periods.

FIG. 14 is a schematic block diagram illustrating one embodiment of apparatus for providing an interpreted recovery score 900 being utilized as a platform for identifying performance periods. Apparatus for providing an interpreted recovery score 900 may include apparatus for providing an interpreted recovery score 702 with movement monitoring module 802 (which can be optional as described above), fatigue level module 804, dynamic recovery profile module 806, and interpreted recovery score module 808, each of which have been described previously. Apparatus for providing an interpreted recovery score 900 may also include initial recovery profile module 902, recovery status module 904, and recovery recommendation module 906, each of which have also been previously described. Additionally, apparatus for providing an interpreted recovery score 900 may further include fitness cycle identification module 1402, and performance period identification module 1404, each of which will be described below in further detail with regard to various processes.

In one embodiment, at least one of (optional) movement monitoring module 802, fatigue level module 804, dynamic recovery profile module 806, interpreted recovery score module 808, initial recovery profile module 902, recovery status module 904, recovery recommendation module 906, fitness cycle identification module 1402, and performance period identification module 1404 are embodied in a wearable sensor, such as electronic capsule 200. In various embodiments, any of the modules described herein may be embodied in electronic capsule 200, and may connect to other modules described herein via communication medium 704. In other embodiments, any of the modules described herein may be embodied in other sensors or devices, e.g., chest heart rate monitor, ear sensor in a headphone device, wristband, armband, etc.

Figure 15:
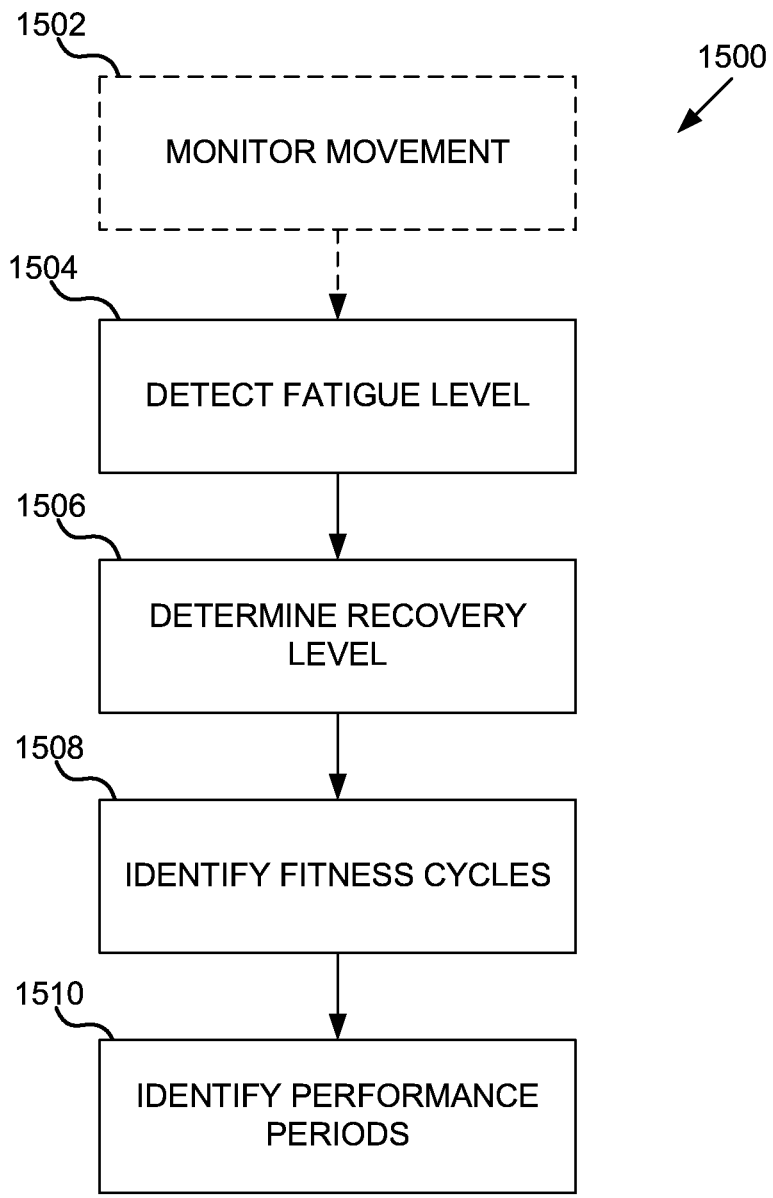
FIG. 15 is an operational flow diagram illustrating an example method for identifying performance periods.

FIG. 15 is an operational flow diagram illustrating example method 1500 for identifying performance periods in accordance with an embodiment of the present disclosure. The operations of method 1500 can utilize information, such as detected fatigue level and, in one embodiment, a user's actual (historical) fatigue, e.g., from learned user characteristics that can be or can include, e.g., a fatigue profile, such as described above, in order to identify fitness cycles and/or present information or data associated with fitness cycles. As a result of identifying fitness cycles, optimal performance periods may also be identified/predicted.

In one embodiment, at operation 1504 (similar to operation 1006 described above), fatigue level may be detected. The fatigue level may be detected in various ways. In one example, the fatigue level is detected solely by measuring HRV of a user using one or more logic circuits 240 (discussed above in reference in to FIG. 1). Fatigue level may be detected more or less frequently, and in accordance with one embodiment, may be detected periodically subsequent to each time some type of stimulus or load indicative of, e.g., some form of exercise or other fitness-related activity, is detected or otherwise determined to have occurred.

In one embodiment, at an optional operation 1502, movement can be monitored in order to identify and/or characterize a stimulus or load placed on the human body of the user, indicating the beginning of a fitness cycle. Optional operation 1502 can monitor movement based on the aforementioned RAT, monitoring movement patterns, intensity, etc. to determine if the movement is indicative of a stimulus associated with, e.g., some fitness-related activity.

In one embodiment, method 1500 may include operation 1506, which involves determining a recovery level. Recovery level can be determined, as described above, from one or more of determining a dynamic recovery profile (similar to operation 1008 described above), and determining an interpreted recovery score (similar to operation 1010 described above).

In one embodiment, at operation 1508, fitness cycles can be identified based upon periods of activity through recovery, as determined through detection of fatigue level, and recovery level (as well as optional movement monitoring) described above, where operation 1508 may be performed by fitness cycle identification module 1402. Accordingly, and based on measured HRV and user history, fatigue level and recovery level can be determined and presented to a user to characterize a fitness cycle progressed through by a user. The presentation of such data may be in a variety of forms, whether numerically, descriptively, or visually, such as in a graph or timeline format. As alluded to previously, providing the user with the awareness of when he or she is moving or has moved through a fitness cycle may allow the user to improve fitness and athletic ability. That is, by training or engaging in activities that provide an optimum fatigue level and waiting for proper recovery before subsequent training or engagement in additional activities overcompensation can occur. Further still, the user can be made aware of his or her athletic or fitness progression by presenting aggregated information or data regarding a plurality of fitness cycles, such as sets of fitness cycles that may be, e.g., contiguous or non-contiguous in time.

It should be noted that in accordance with other embodiments, the detection of fatigue, as well as movement monitoring (when optionally utilized), may be tailored or focused on a particular type of activity, sets of activity, etc. For example, a user may wish to identify fitness cycles relevant to cycling activities rather than weight-lifting activities. Alternatively, the user may wish to gather and/or aggregate data regarding sets of one or more activities associated with a workout session, for example. For example, in one embodiment, identify fitness cycles module 1402 may aggregate various stimuli detected by optional movement monitoring module 802 (and associated with a workout session), determine an aggregate fatigue level resulting from the various stimuli, and identify and/or present fitness cycles commensurate with the workout session and resulting recovery.

It should be further noted that presentation of fitness cycle information can be accomplished in variety of ways. For example, fitness cycle information can be presented in a visual/graphical manner, similar to that illustrated in FIGS. 13A and 13B. Alternatively or in addition to such visual representations, fitness cycles information can be quantified and/or otherwise described and presented to a user in a textual, numerical, or descriptive manner.

In one embodiment, at operation 1510, performance periods may be identified or predicted, where operation 1510 may be performed by performance period identification module 1404. For example, and depending upon when a fitness cycle has been identified or occurs, an optimal performance period may be predicted by determining periods residing within fitness cycles.

As described above, HRV or HRV in combination with metrics, can be used to calculate a fatigue level. For example, the logic circuits may detect the amount of physical activity and the amount of sleep a user experienced over the last 48 hours, combine those metrics with the user's HRV, and calculate a fatigue level of between 1 and 10, wherein the fatigue level could indicate the user's physical condition and aptitude for further physical activity that day. The fatigue level may also be calculated on a scale of between 1 and 100, or any other scale or range. In one embodiment, the typical fatigue level ranges from about 40 to 60. The fatigue level may also be represented on a descriptive scale; for example, low, normal, and high.

Additionally, as also described above, an interpreted recovery score, because it is based on both the fatigue level detected and on actual, historical results (as incorporated into the dynamic recovery profile), provides higher resolution and additional perspective into the user's current performance state. In one embodiment, the interpreted recovery score supplements the fatigue level with information to account for the user's past activities from the archive, for example, (i.e. learned user characteristics). The interpreted recovery score may be, for example, a number selected from a range of numbers, and again, in one case, the interpreted recovery score may be proportional to the fatigue level, where a typical interpreted recovery score ranges from 40 to 60.

Depending on how performance periods may be designated or defined (which can be configured, e.g., at some default designation(s), value(s), range(s), or tailored to a particular user(s)), a performance period may be associated with a particular fatigue level. For example, a fatigue level between the range of 40 to 60 may be considered to be a period of recovery, which can be correlated to or interpreted/identified as a performance period. That is, a fatigue level of 30 may be indicative that a user is still too fatigued, while a fatigue level in the range of 60 to 80 may be indicative that the user is fresh/fully recovered. Accordingly, performance periods, in one embodiment, can be regarded as periods of optimal performance/activity that can result in a trend of proper overcompensation, which over time can result increased fitness levels.

Periods of optimal performance, as determined or predicted at operation 1510 may be presented or identified to a user in at least one of a numerical, descriptive, or visual manner. Moreover, the presentation or identification of such periods of optimal performance can be performed separately from or commensurate with the presentation of data associated with or characterizing the fitness cycles described above. For example, and in accordance with one embodiment, when a plurality of fitness cycles are illustrated to the user in a graphical format (e.g., fitness level as a function of time), visual indicators may be placed within illustrated fitness cycles to indicate optimal performance periods.

In one embodiment, the operations of method 1000, method 1100, method 1200, and method 1500 are performed using sensors configured to be attached to the body (e.g., the user's body). Such sensors may include a gyroscope or accelerometer to detect movement, and a heart-rate sensor, each of which may be embedded in a wristband that a user can wear on the user's wrist or ankle, such as wristband 100, or a device or module such as electronic capsule 200. Such sensors may be used to perform the operations of monitoring the movement, detecting the fatigue level, creating and updating the dynamic recovery profile, and creating and updating the interpreted recovery score, or any other operation disclosed herein. In further embodiments, sensors used to perform these operations may be standalone sensors, and may not attach to the body.

Figure 16:
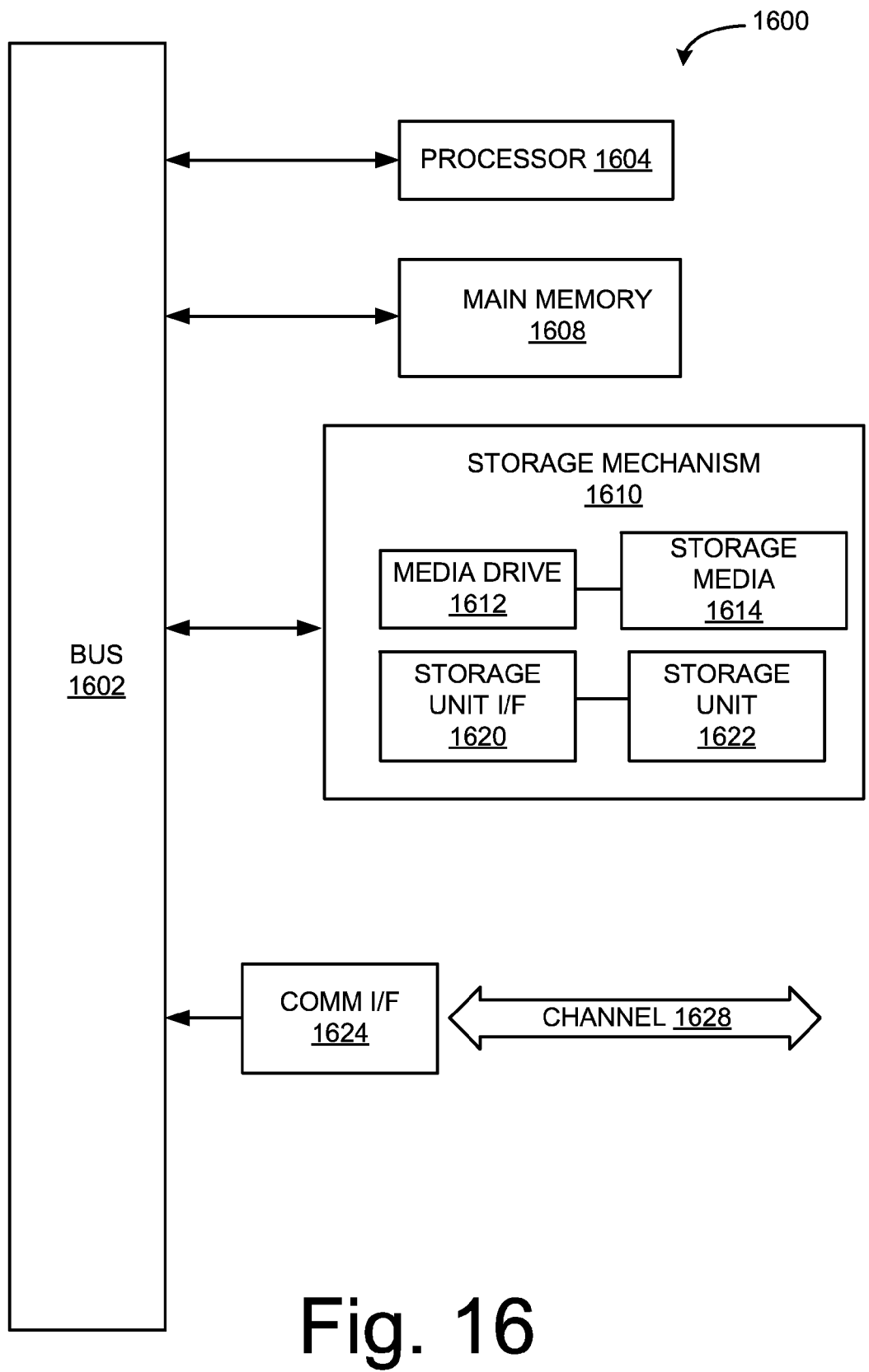
FIG. 16 illustrates an example computing module that may be used to implement various features of the systems and methods disclosed herein.

FIG. 16 illustrates an example computing module that may be used to implement various features of the systems and methods disclosed herein. In one embodiment, the computing module includes a processor and a set of computer programs residing on the processor. The set of computer programs is stored on a non-transitory computer readable medium having computer executable program code embodied thereon. The computer executable code is configured to monitor a movement to create a metabolic activity score based on the movement and user information. The computer executable code is further configured to detect a fatigue level. The computer executable code is also configured to create and update a dynamic recovery profile based on an archive. The archive may include historical information about the movement, the metabolic activity score and the fatigue level. The computer executable codes is further configured to create and update an interpreted recovery score based on the fatigue level and the dynamic recovery profile. The computer executable codes is configured, further still, to identify fitness cycles and performance periods.

The example computing module may be used to implement these various features in a variety of ways, as described above with reference to the methods illustrated in FIGS. 10A, 11,12, and 15, and as will be appreciated by one of ordinary skill in the art.

As used herein, the term module might describe a given unit of functionality that can be performed in accordance with one or more embodiments of the present application. As used herein, a module might be implemented utilizing any form of hardware, software, or a combination thereof. For example, one or more processors, controllers, application-specific integrated circuits (ASICs), programmable logic arrays (PLAs), Programmable Array Logic (PAL) devices, complex programmable logic devices (CPLDs), field-programmable gate arrays (FPGAs), logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 16. Various embodiments are described in terms of this example—computing module 1600. After reading this description, it will become apparent to a person skilled in the relevant art how to implement the application using other computing modules or architectures.

Referring now to FIG. 16, computing module 1600 may represent, for example, computing or processing capabilities found within desktop, laptop, notebook, and tablet computers; hand-held computing devices (tablets, personal digital assistants (PDAs), smart phones, cell phones, palmtops, smart-watches, smart-glasses etc.); mainframes, supercomputers, workstations or servers; or any other type of special-purpose or general-purpose computing devices as may be desirable or appropriate for a given application or environment. Computing module 1600 might also represent computing capabilities embedded within or otherwise available to a given device. For example, a computing module might be found in other electronic devices such as, for example, digital cameras, navigation systems, cellular telephones, portable computing devices, modems, routers, Wireless Application Protocol (WAP) devices, terminals and other electronic devices that might include some form of processing capability.

Computing module 1600 might include, for example, one or more processors, controllers, control modules, or other processing devices, such as a processor 1604. Processor 1604 might be implemented using a general-purpose or special-purpose processing engine such as, for example, a microprocessor, controller, or other control logic. In the illustrated example, processor 1604 is connected to a bus 1602, although any communication medium can be used to facilitate interaction with other components of computing module 1600 or to communicate externally.

Computing module 1600 might also include one or more memory modules, simply referred to herein as main memory 1608. For example, preferably random access memory (RAM) or other dynamic memory, might be used for storing information and instructions to be executed by processor 1604. Main memory 1608 might also be used for storing temporary variables or other intermediate information during execution of instructions to be executed by processor 1604. Computing module 1600 might likewise include a read only memory (ROM) or other static storage device coupled to bus 1602 for storing static information and instructions for processor 1604.

The computing module 1600 might also include one or more various forms of information storage mechanism 1610, which might include, for example, a media drive 1612 and a storage unit interface 1620. The media drive 1612 might include a drive or other mechanism to support fixed or removable storage media 1614. For example, a hard disk drive, a solid state drive, a magnetic tape drive, an optical disk drive, a CD or DVD drive (R or RW), or other removable or fixed media drive might be provided. Accordingly, storage media 1614 might include, for example, a hard disk, a solid state drive, magnetic tape, cartridge, optical disk, a CD or DVD, or other fixed or removable medium that is read by, written to or accessed by media drive 1612. As these examples illustrate, the storage media 1614 can include a computer usable storage medium having stored therein computer software or data.

In alternative embodiments, information storage mechanism 1610 might include other similar instrumentalities for allowing computer programs or other instructions or data to be loaded into computing module 1600. Such instrumentalities might include, for example, a fixed or removable storage unit 1622 and a storage interface 1620. Examples of such storage units 1622 and storage interfaces 1620 can include a program cartridge and cartridge interface, a removable memory (for example, a flash memory or other removable memory module) and memory slot, a Personal Computer Memory Card International Association (PCMCIA) slot and card, and other fixed or removable storage units 1622 and storage interfaces 1620 that allow software and data to be transferred from the storage unit 1622 to computing module 1600.

Computing module 1600 might also include a communications interface 1624. Communications interface 1624 might be used to allow software and data to be transferred between computing module 1600 and external devices. Examples of communications interface 1624 might include a modem or soft modem, a network interface (such as an Ethernet, network interface card, WiMedia, Institute of Electrical and Electronic Engineers (IEEE) 802.XX or other interface, a communications port (such as for example, a USB port, infrared (IR) port, RS-232 port, BLUETOOTH® interface, or other port), or other communications interface. Software and data transferred via communications interface 1624 might typically be carried on signals, which can be electronic, electromagnetic (which includes optical) or other signals capable of being exchanged by a given communications interface 1624. These signals might be provided to communications interface 1624 via a channel 1628. This channel 1628 might carry signals and might be implemented using a wired or wireless communication medium. Some examples of a channel might include a phone line, a cellular link, a radio frequency (RF) link, an optical link, a network interface, a local or wide area network, and other wired or wireless communication channels.

In this document, the terms "computer program medium" and "computer usable medium" are used to generally refer to transitory or non-transitory media such as, for example, memory 1608, storage unit 1620, media 1614, and channel 1628. These and other various forms of computer program media or computer usable media may be involved in carrying one or more sequences of one or more instructions to a processing device for execution. Such instructions embodied on the medium are generally referred to as "computer program code" or a "computer program product" (which may be grouped in the form of computer programs or other groupings). When executed, such instructions might enable the computing module 1600 to perform features or functions of the present application as discussed herein.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

What is claimed is:

1. An apparatus for identifying a performance period, comprising:
   one or more sensors configured to be worn by a user, the one or more sensors configured to monitor movement of the user associated with a fitness activity;
   a fitness cycle identification module that is configured to identify progression of the user through a plurality of fitness cycles based on signals from the one or more sensors, each of the plurality of fitness cycles encompassing a period from a beginning of a stimulus associated with the fitness activity through recovery from the stimulus; and
   a performance period identification module that is configured to predict optimal performance periods for the user to begin performing the fitness activity based on data collected by the one or more sensors during the plurality of fitness cycles and data collected relating to a current fatigue level of the user.

2. The apparatus of claim 1, wherein the one or more sensors includes a heart rate variability sensor that is adapted to provide at least a portion of the data used to determine the current fatigue level of the user.

3. The apparatus of claim 2, further comprising a recovery module that determines a recovery level based at least in part, on the current fatigue level of the user.

4. The apparatus of claim 2, further comprising an archive for storing a set of one or more learned user characteristics including at least a fatigue profile of a user.

5. The apparatus of claim 4, further comprising a recovery module that determines a recovery level based at least in part, on the current fatigue level of the user, wherein the recovery module is configured to determine the recovery level based upon heart rate variability and the set of one or more learned user characteristics.

6. The apparatus of claim 1, wherein the fitness cycle identification module is further configured to present data associated with the plurality of fitness cycles in at least one of a numerical, descriptive, or visual manner.

7. The apparatus of claim 6, wherein the fitness activity comprises cycling, running or walking.

8. The apparatus of claim 1, wherein the performance period identification module is configured to predict the optimal performance periods by determining periods of time predicted to occur within each of the plurality of fitness cycles during which experiencing additional stimuli promotes future increased fitness levels.

9. A method of identifying a performance period, comprising:
   monitoring movement of a user by using a first sensor worn by the user;
   determining the user is performing a fitness activity based on signals from the first sensor;
   determining heart rate variability data of the user by using a second sensor worn by the user;
   identifying one or more fitness cycles of the user, each fitness cycle comprising a period of time beginning from a stimulus associated with the fitness activity and progressing through recovery from fatigue experienced in response to the stimulus associated with the fitness activity and each fitness cycle is identified based on the monitored movement of the user, the heart rate variability data and a set of one or more learned user characteristics;
   determining an optimal performance period for the user to begin performing the fitness activity based on data collected by the second sensor during the one or more fitness cycles and data collected relating to a current fatigue level of the user; and
   performing the fitness activity by the user during the optimal performance period.

10. The method of claim 9, wherein the data relating to the current fatigue level is determined based on the heart rate variability data of the user.

11. The method of claim 10, wherein the determining of the optimal performance period comprises determining a period during which the current fatigue level experienced falls within a range of fatigue level values corresponding to a period of recovery within one of the one or more the fitness cycles.

12. The method of claim 10, further comprising determining a recovery level based at least in part, on the current fatigue level.

13. The method of claim 12, further comprising periodically detecting the current fatigue level to determine the recovery level.

14. The method of claim 9, further comprising presenting data associated with the fitness cycle in at least one of a numerical, descriptive, or visual manner.

15. The method of claim 14, further comprising presenting data associated with the optimal performance period in conjunction with the data associated with the fitness cycle.

16. A system for identifying a performance period, comprising:
   a first sensor configured to be worn by a user, the first sensor configured to monitor movement of the user associated with a fitness activity;
   a second sensor configured to monitor a heart rate variability of the user
   a processor; and
   a non-transitory computer readable medium including computer program code, the non-transitory computer readable medium and the computer program code adapted to, with the processor, cause the system to:
   monitor movement of a user by using the first sensor worn by the user;
   determine the user is performing a fitness activity based on signals received from the first sensor;
   detect a current fatigue level associated with fatigue experienced in response to the fitness activity;
   determine a recovery level based at least in part, on the current fatigue level;
   identify one or more fitness cycles, each fitness cycle comprising a segment of time beginning from a stimulus associated with the fitness activity and progressing through recovery from the fatigue experienced in response to the stimulus;

predict an optimal performance period for the user to begin performing the fitness activity based on data collected during the one or more fitness cycles and data collected relating to a current fatigue level of the user; and determine the user is performing the fitness activity during the optimal performance period based on signals received from the first sensor.

17. The system of claim 16, wherein the non-transitory computer readable medium and the computer program code are adapted to, with the processor, cause the system to detect the fatigue level and determine recovery level based on heart rate variability data and a set of one or more learned user characteristics.

18. The system of claim 16, wherein the non-transitory computer readable medium and the computer program code are adapted to, with the processor, further cause the system to present data associated with the fatigue level, and the recovery level to characterize the identified fitness cycle in at least one of a numerical, descriptive, or visual manner.

19. The system of claim 16, wherein the non-transitory computer readable medium and the computer program code are adapted to, with the processor, further cause the system to present data associated with the optimal performance period in conjunction with the data characterizing the identified fitness cycle.

* * * * *